(12) United States Patent
Hetts et al.

(10) Patent No.: US 11,406,485 B2
(45) Date of Patent: Aug. 9, 2022

(54) IN VIVO POSITIONABLE FILTRATION DEVICES AND METHODS RELATED THERETO

(71) Applicant: The Regents of the University of California, Oakland, CA (US)

(72) Inventors: Steven W. Hetts, Hillsborough, CA (US); Anand S. Patel, San Francisco, CA (US); Mark W. Wilson, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 189 days.

(21) Appl. No.: 14/649,838

(22) PCT Filed: Dec. 18, 2013

(86) PCT No.: PCT/US2013/076159
§ 371 (c)(1),
(2) Date: Jun. 4, 2015

(87) PCT Pub. No.: WO2014/100201
PCT Pub. Date: Jun. 26, 2014

(65) Prior Publication Data
US 2015/0305850 A1    Oct. 29, 2015

Related U.S. Application Data

(60) Provisional application No. 61/784,507, filed on Mar. 14, 2013, provisional application No. 61/745,183, filed on Dec. 21, 2012.

(51) Int. Cl.
*A61F 2/01*    (2006.01)
*A61M 1/36*    (2006.01)
(Continued)

(52) U.S. Cl.
CPC .......... *A61F 2/013* (2013.01); *A61M 1/3615* (2014.02); *A61F 2/011* (2020.05); *A61F 2/0105* (2020.05);
(Continued)

(58) Field of Classification Search
CPC ...... A61F 2/013; A61F 2/01; A61F 2002/011; A61F 2002/016; A61F 2230/0063;
(Continued)

(56) References Cited

U.S. PATENT DOCUMENTS

| 5,800,517 A | 9/1998 | Anderson et al. |
| 8,246,565 B2 | 8/2012 | Hyde et al. |

(Continued)

FOREIGN PATENT DOCUMENTS

| CN | 101491465 | 7/2009 |
| JP | 2011517592 | 6/2011 |

(Continued)

*Primary Examiner* — Kevin C Sirmons
*Assistant Examiner* — Alexandra Lalonde
(74) *Attorney, Agent, or Firm* — Thomas |Horstemeyer, LLP

(57) ABSTRACT

In vivo positionable filtration devices are provided that filter one or more therapeutic agents in blood flowing in a blood vessel. The filtration devices include an elongated member and a filtering component coupled to the elongated member. The elongated member and the filtering component are dimensioned for positioning within the blood vessel of a human or non-human animal. Further, the filtering component includes a filtration material to filter the one or more therapeutic agents from the blood. Methods of in vivo filtration of the one or more therapeutic agents are also provided. The methods include positioning a filtration device in the blood vessel of a body of the human or non-human animal, and administering a therapeutic agent upstream from a target tissue site to direct flow of the (Continued)

therapeutic agent to the target tissue site and then to the filtration device. The filtration device is positioned downstream from the target tissue site.

20 Claims, 20 Drawing Sheets

(51) Int. Cl.
*A61M 25/10* (2013.01)
*A61M 25/00* (2006.01)

(52) U.S. Cl.
CPC ....... *A61F 2/0108* (2020.05); *A61F 2002/015* (2013.01); *A61F 2230/0067* (2013.01); *A61M 1/3679* (2013.01); *A61M 25/0029* (2013.01); *A61M 2025/1052* (2013.01); *A61M 2025/1097* (2013.01)

(58) Field of Classification Search
CPC .......... A61F 2002/018; A61F 2002/015; A61F 2230/0006; A61F 2230/0067; A61F 2230/008; A61F 2/0108; A61M 1/3679; A61M 1/3615; A61M 2025/1097; A61M 1/3601; A61M 1/3621; A61M 1/3627; A61M 1/34; A61M 1/3633; A61M 1/3635; A61M 1/3636; A61M 25/00; A61M 25/003; A61M 25/0067; A61M 25/007; A61M 25/0029; A61M 2205/125; A61M 2205/126; A61M 2205/75; A61M 2205/7509; A61M 2025/1052; B01D 2325/02; B01D 69/02; A61B 17/22031
See application file for complete search history.

(56) References Cited

U.S. PATENT DOCUMENTS

| | | | |
|---|---|---|---|
| 2002/0062133 A1 | 5/2002 | Gilson et al. | |
| 2002/0091407 A1* | 7/2002 | Zadno-Azizi | A61B 17/22 606/200 |
| 2002/0161394 A1* | 10/2002 | Macoviak | A61F 2/01 606/200 |
| 2004/0006367 A1* | 1/2004 | Johnson | A61B 17/22031 606/200 |
| 2004/0064099 A1* | 4/2004 | Chiu | A61F 2/013 604/164.01 |
| 2004/0158275 A1* | 8/2004 | Crank | A61F 2/013 606/200 |
| 2004/0167564 A1* | 8/2004 | Fedie | A61F 2/013 606/200 |
| 2006/0149312 A1* | 7/2006 | Arguello | A61F 2/013 606/200 |
| 2006/0177478 A1 | 8/2006 | Humes et al. | |
| 2008/0058758 A1* | 3/2008 | Ranchod | A61M 25/007 604/508 |
| 2008/0213523 A1* | 9/2008 | Fujimoto | A61M 1/3627 428/36.5 |
| 2010/0268199 A1* | 10/2010 | Hyde | A61M 1/362 604/891.1 |
| 2010/0316694 A1 | 12/2010 | Mousa et al. | |
| 2011/0137399 A1* | 6/2011 | Chomas | A61F 2/013 623/1.12 |
| 2011/0282274 A1* | 11/2011 | Fulton, III | A61M 1/367 604/28 |
| 2012/0035434 A1* | 2/2012 | Ferren | A61B 1/00156 600/301 |
| 2012/0265118 A1 | 10/2012 | Solomon et al. | |
| 2013/0131423 A1* | 5/2013 | Wang | A61M 1/3486 600/1 |
| 2014/0188248 A1* | 7/2014 | Gandhi | B01J 41/13 623/23.66 |

FOREIGN PATENT DOCUMENTS

| | | | |
|---|---|---|---|
| WO | WO 96/19941 | 2/1999 | |
| WO | WO 01/067989 | 9/2003 | |
| WO | WO 2004/083817 | 9/2006 | |
| WO | 2011/112463 | 9/2011 | |
| WO | 2011/133287 | 10/2011 | |
| WO | WO 2012120490 A2 * | 9/2012 | ........... A61B 17/221 |

* cited by examiner

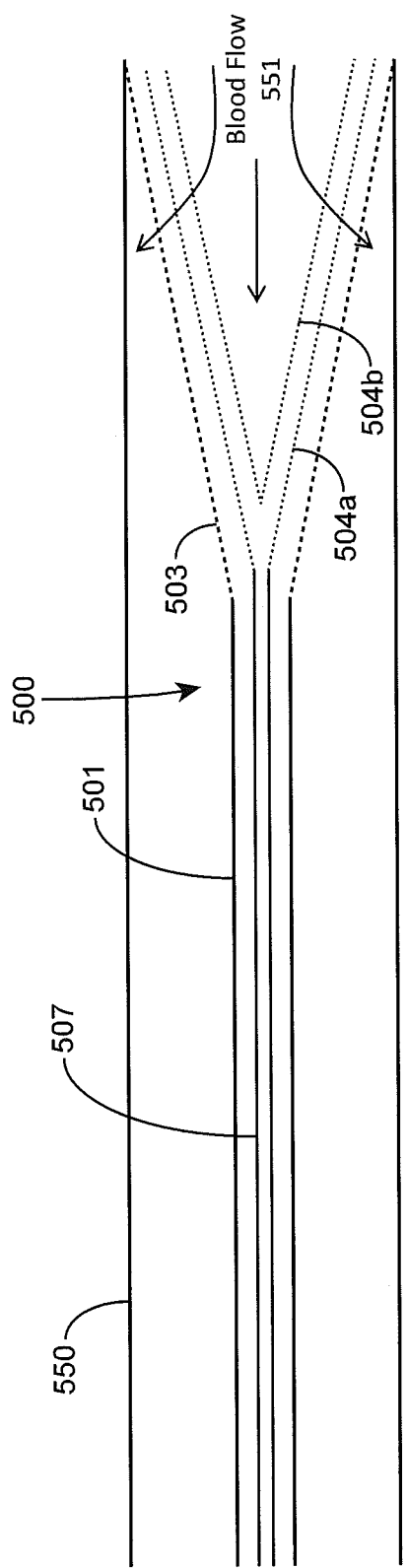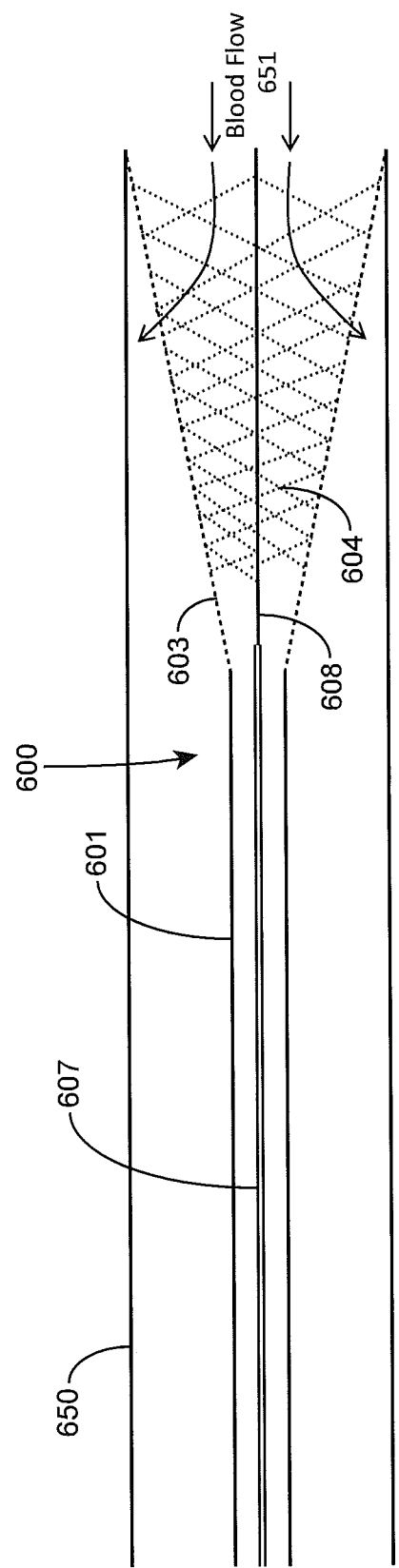
FIG. 5
FIG. 6

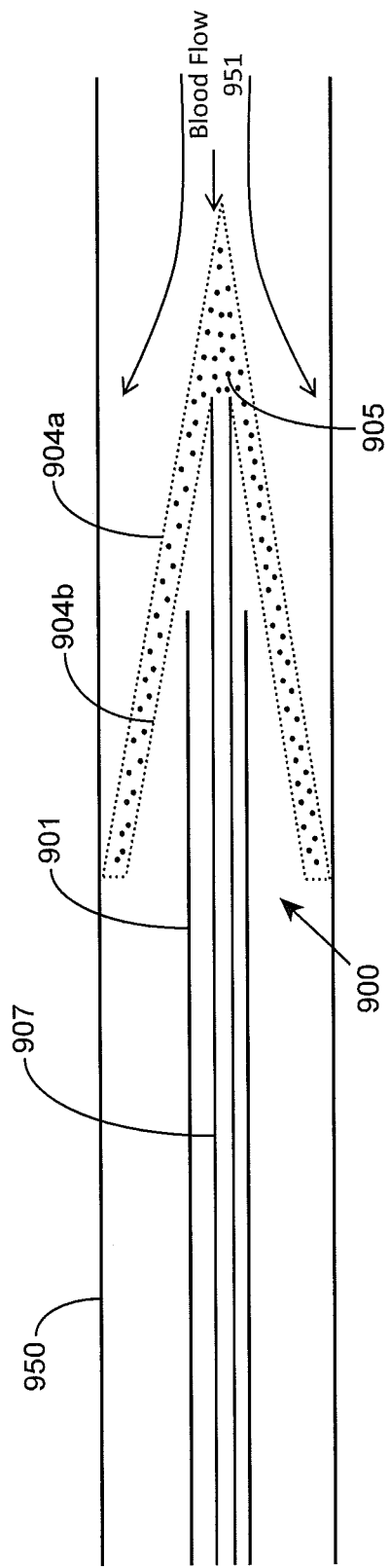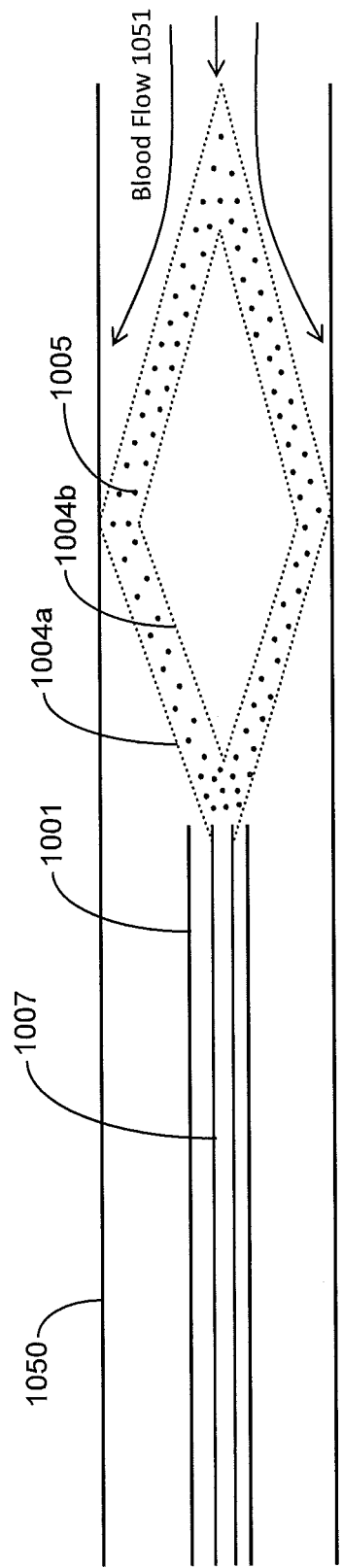

IN VIVO POSITIONABLE FILTRATION DEVICES AND METHODS RELATED THERETO

CROSS-REFERENCE

This application claims the benefit of U.S. Provisional Patent Application No. 61/745,183 filed Dec. 21, 2012, and U.S. Provisional Patent Application No. 61/784,507 filed Mar. 14, 2013, which applications are incorporated herein by reference in their entirety.

STATEMENT REGARDING FEDERALLY SPONSORED RESEARCH

This invention was made with government support under grant no. TR000004 awarded by the National Institutes of Health. The government has certain rights in the invention.

INTRODUCTION

In vivo positionable filtration devices are provided that filter one or more therapeutic agents in blood flowing in a blood vessel. The filtration devices include an elongated member and a filtering component coupled to the elongated member. The elongated member and the filtering component are dimensioned for positioning within a blood vessel of a human or non-human animal. Further, the filtering component includes a filtration material to filter the one or more therapeutic agents from blood. Methods of in vivo filtration of one or more therapeutic agents are also provided. The methods include positioning a filtration device in a blood vessel of a body of a human or non-human animal, and administering a therapeutic agent upstream from the target tissue site to direct flow of the therapeutic agent to the target tissue site and then to the filtration device. The filtration device is positioned downstream from a target tissue site.

SUMMARY

In some aspects of the present disclosure, in vivo positionable filtration devices are provided that filter one or more therapeutic agents in blood flowing in a blood vessel. The filtration devices include an elongated member and a filtering component coupled to the elongated member. The elongated member and the filtering component are dimensioned for positioning within a blood vessel of a human or non-human animal. Further, the filtering component includes a filtration material to filter the one or more therapeutic agents from blood.

In some aspects of the present disclosure, methods of in vivo filtration of one or more therapeutic agents are provided. The methods include positioning a filtration device in a blood vessel of a body of a human or non-human animal, and administering a therapeutic agent upstream from the target tissue site to direct flow of the therapeutic agent to the target tissue site and then to the filtration device. The filtration device is positioned downstream from a target tissue site. Further, the filtration device is for filtering the therapeutic agent in the blood flowing in the blood vessel. The in vivo positioned filtration device filters the therapeutic agent as the blood and the therapeutic agent are received by the filtration device.

BRIEF DESCRIPTION OF THE FIGURES

FIGS. 3-10 illustrate exemplary filtration devices according to different embodiments;

DETAILED DESCRIPTION

Figure 1:
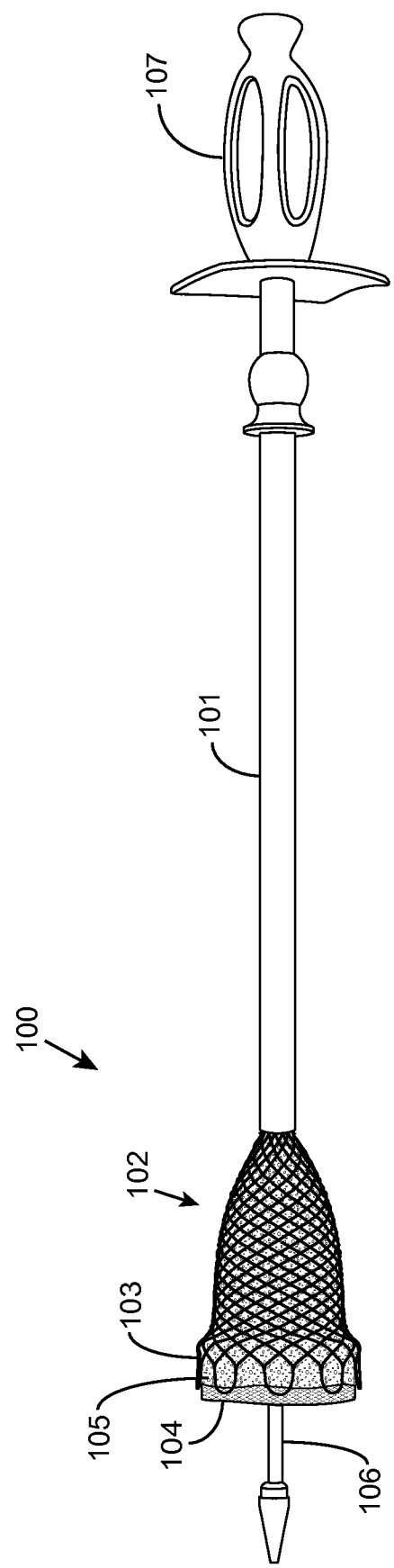
FIG. 1 illustrates a side view of an in vivo positionable filtration device, according to one embodiment.

Cancer is currently the second leading cause of death in the United States and is on course to exceed cardiovascular disease as the leading cause of death in the next decade. Conventional intravenous chemotherapy is dose-limited by systemic toxicity. A common chemotherapeutic used for a variety of tumors is doxorubicin (Dox), whose toxicities include bone marrow suppression, gastrointestinal damage, and perhaps most notoriously irreversible cardiac failure.

In order to limit these systemic toxicities and also further increase chemotherapeutic dose to the cancer, for certain tumors such as those in the liver for instance, a chemotherapeutic agent such as Dox may be administered intraarterially directly into the vessels feeding the tumor. However, large percentages of the chemotherapeutic agent may pass directly through the tumor into the systemic venous circulation.

In some aspects, an in vivo positionable filtration device is provided to capture or otherwise filter therapeutic agents that pass through a target tissue site (e.g., a cancerous site). The filtering of the therapeutic agent may facilitate optimization of chemotherapy dosages, for example, and minimize systemic toxicity levels of the chemotherapeutic agent. While the devices and methods of the present disclosure are described with respect to cancer and chemotherapeutic agents, such as Dox, it should be appreciated that non-chemotherapeutic agents may also be applicable for cancerous and non-cancerous conditions, diseases, illnesses, etc.

Devices

In some aspects of the present disclosure, in vivo positionable filtration devices are provided that filter one or more therapeutic agents in blood flowing in a blood vessel. The filtration devices include an elongated member and a filtering component coupled to the elongated member. The elongated member and the filtering component are dimensioned for positioning within a blood vessel of a human or non-human animal. Further, the filtering component includes a filtration material to filter the one or more therapeutic agents from blood.

The filtration material may include a material that filters one or more therapeutic agents from the blood. The therapeutic agents may be, for example, chemotherapeutic agents or non-chemotherapeutic agent may be implemented. In one embodiment, the chemotherapeutic agent is Dox.

It should be appreciated that the term "therapeutic agent" is used broadly herein and may include therapeutic particles. Furthermore, references to "filtering of a therapeutic agent" are used broadly herein and encompass the filtering of therapeutic particles. For example, in certain embodiments, particles may include free chemotherapy (or non-chemotherapy) molecules, or chemotherapy (or non-chemotherapy) loaded molecules (e.g., chemotherapy molecules that are bound to particles such as drug eluting resins or drug eluting activated carbon). Exemplary therapeutic agents include, but are not limited to: chemotherapy agents; vasoactive agents, e.g. verapamil, nicardipine, or milrinone; Sodium tetradecyl sulfate (Sotradecol, Angiodynamics or BioNiche Pharmaceuticals); bleomycin; X-ray or MRI contrast agents; antibiotics; lytic agents (for example, and clot dissolving drugs such as tPA). In certain embodiments, the particles may include bland particles. Particles may include, for example, particles that occlude blood vessels of cancerous or otherwise diseased tissue. In some instances, particles may include polymers, glues, resins, activated carbon, or glass. In certain embodiments, the particles may be bound to radiation emitting isotopes, such as radiotherapeutic particles.

The filtration material may include a material that has properties that adsorb, bind, trap, or inactivate or degrade the therapeutic agent. For instance, in certain embodiments, the filtration material may include beads or other particles that adsorb, bind, trap, or inactivate or degrade the therapeutic agent.

As stated above, in certain embodiments, the filtration material may filter a therapeutic agent from the blood by adsorbing or binding to the therapeutic agent to enable removal from the blood. For example, the filtration material may possess properties that adsorb a therapeutic agent, chemically bind to a therapeutic agent, and/or magnetically bind to a magnetic carrier of the therapeutic agent, without significant binding or filtration of endogenous entities in the blood. The binding between the filtration material and the therapeutic agent may be irreversible or weakly reversible. In this way, the therapeutic agent may be collected by the filtration material and removed from the blood.

The percentage of therapeutic agent removed may vary in different embodiments based on the specific filtration material, therapeutic agent, and filtration device configuration. In certain embodiments, for example, the percentage of therapeutic agent removed by the filtration material may range from 50% or greater, such as 80% or greater, including 95% or greater.

In one embodiment, the filtration material includes a resin that has properties that adsorbs a therapeutic agent, chemically binds to a therapeutic agent, and/or magnetically binds to a magnetic carrier bound to a therapeutic agent. Example filtration materials including resins having properties to adsorb and/or chemically bind to a therapeutic agent such as doxorubicin, may include, but are not limited to: strong acid cation exchange polymer resins; ion exchange resins; polymeric adsorbent resins without ion exchange; resins including sulfonate groups that ionically bond to the therapeutic agent; chromatography based resins, acrylic-based resins including those composed of polyacrylamide, polyacrylic acid, sodium acrylate and even vinyl copolymers, or any combination thereof. Such resins could be incorporated onto a membrane or sheet made from polymers or cloth, with examples including Nafion (Dupont), Neosepta, CMI-7000 (Membranes International), and IONAC membranes (Sybron Chemicals).

For example, in one embodiment, a strong acid cation exchange polymer resins may be used for a mildly positively charged drug such as Dox. Other examples of compounds that chemically or physically (via adsorption) bind to a therapeutic agent such as doxorubicin, may include, but are not limited to: calsequestrin; cyclic oligosaccharides, such as cyclodextrins, including gamma-cyclodextrin; hNopp140; antibodies that specifically bind the agent, such as an anti-doxorubicin monoclonal antibody (MAD 11); nucleolar phosphoprotein; *Clostridium botulinum* neurotoxin B; cell membrane lipids such as cardiolipin, phophatidylserine, and phosphatic acid; nucleic acid ligands so called 'aptamers' including RNA and DNA; albumin; and hemoglobin.

Further, it should be appreciated that in other embodiments, various other types of ion exchange resins may be applicable, including, but not limited to, weak-acid cation exchange, weak-base anion exchange, strong-base anion exchange. For instance, in one embodiment, for a negatively charged drug (e.g., heparin), a strong-base anion exchange resin is implemented.

Factors such as resin functional group and porosity/cross-linking, solution temperature, pH, concentration, and ionic strength may factor into the effectiveness of the resin to bind to the therapeutic agent. In some instances, for example, cyanogen bromide activation of resins may be used to attach functional groups. In certain instances, a low cross-linked version of these resins is implemented, such as 3% or less, including 2% or less. Higher cross-linked versions are also applicable and may also be implemented.

In certain embodiments, the filtration material includes carbon such as activated carbon (e.g., charcoal or activated charcoal) that binds to the therapeutic agent. The effectiveness of the activated carbon may vary based on factors such as pore size, shape, surface area, ash content, and hardness, for example. In some instances, the carbon may be coated with additional resin material. Furthermore, carbons and resins are inexpensive and small amounts may be used and still be effective. While larger amounts may be implemented in some instances, example amounts of carbons and resin, such as 10 grams or less, such as 5 grams or less, and including 1 gram or less, may be implemented and be effective.

Example resins for the filtration device may include, but are not limited to, one or more of the following: HepaSphere, QuadraSphere, Dowex 50W-X2; Dowex 50W-X4; Dowex 50W-X8; Biorad AG50W-X2; Biorad AG50W-X4; Biorad AG50W-X8; GE Sepharose Big Beads; Amberlite XAD-2; Tosoh Toyopearl MegaCap II; Purolite PAD 600; and Purolite CGC100X2. Example carbons for the filtration device may include, but are not limited to, one or more of the following: Norit C Gran; Calgon TOG NDS 20×50; and QUO-YC-1041.

In certain embodiments, the filtration material may include a material that improves biocompatibility, such as polymethyl-methacrylate (PMMA), chitosan, heparin, etc. In some instances, for example, the resin or carbon of the filtration material may be coated or otherwise impregnated with the PMMA, chitosan, and/or heparin. Example coating methods may be found in U.S. Patent Publication No. 2010/0316694, the entirety of which is incorporated herein by reference.

In certain embodiments, the filtration material may filter a therapeutic agent from the blood by inactivating or otherwise degrading the therapeutic agent or the toxicity of the therapeutic agent. For example, the filtration material may be a catalytic material, such as an immobilized (covalently or non-covalently) enzyme that, for example, enzymatically degrades the therapeutic agent to reduce its toxicity level. Enzymatic degradation and inactivation of Dox, for example, may occur via cleavage of its sugar backbone with glycosidases contained in the liver.

In other embodiments, the therapeutic agent administered to the patient may be pretreated by covalently or non-covalently associating the compound with a magnetic particle, such as a magnetic nanoparticle. Accordingly, the filtration material may be composed of a magnetic material so that following treatment the magnetically bound therapeutic particle may be attracted to the magnetic material of the filtration material.

In yet other embodiments, the filtration material is composed of basic mechanical sieve-like filter which traps a wide range of particles that are commonly used to embolize tumors, such as resin based particles, such as DC Beads and LC Beads (ion-exchange resins), QuadraSpheres and Hepa-Spheres (sodium acrylate and vinyl copolymer resin), EmboSpheres (tris-acryl resins), Bead Block and Cotonour Beads (polyvinyl alcohol resins), Onyx (ethylene vinyl copolymer, EVOH), TruFill or Histacryl (n-butyl-cyanoacrylate (nBCA) compounds), embolization coils, or activated carbon particles. Such particles may or may not be loaded with a therapeutic agent that would elute in the tumor. In such exemplary embodiments, the filtration material will trap these particles out of the exiting venous blood stream to prevent them from depositing in non-target organs. Moreover, the filtration material of such embodiments could simultaneously be composed of a chemical based binding filtration mechanism to filter out free drug from the blood as well.

The reduction of the toxicity level may vary based on the selected filtration material, therapeutic agent, and specific filtration device configuration. In certain embodiments, the reduction of toxicity level ranges from 50% or greater, such as 75% or greater, including 90% or greater.

While parts of the present disclosure are described with respect to a filtration material having properties that either adsorb, bind, trap, or inactivate (or degrade) the therapeutic agent, it is appreciated that in some embodiments, the filtration material may include a combination of these properties. In some instances, for example, the filtration material may include one or more materials having properties that adsorb, bind, trap, or inactivate (or degrade) the therapeutic agent. For example, parts of the present disclosure may be described with respect to a filtration material including resin, carbon, or catalytic material. It is appreciated that in some embodiments, the filtration material may include any combination of resin, carbon, and catalytic materials. Furthermore, the filtration material may include more than one type of resin, carbon, or catalytic material. In some instances, for example, the filtration material may include one or more materials that trap particles, such as by mechanically trapping particles based on a pore size of a filter being smaller than the size of the particle.

Still further, the filtration material may include a material to improve biocompatibility, such as including but not limited to one or more of the following: PMMA, chitosan, heparin, citrate, and ethylenediaminetetraacetic acid (EDTA). For example, the filtration material may include a resin coated with heparin and an activated carbon coated with chitosan. Moreover, the filtration material may be applicable to more than one therapeutic agent—e.g., filter more than one chemotherapeutic agent, filter more than one non-chemotherapeutic agent, or filter a combination of chemotherapeutic and non-chemotherapeutic agents. For example, the filtration material may include a resin that chemically binds to one chemotherapeutic agent and activated carbon that binds to another chemotherapeutic agent.

References may be made herein to a proximal and distal end of the filtration device or components therein. The term "proximal" is used here to refer generally to the end or side of the filtration device or component thereof that is closer to the operator of the device (e.g., physician) than to the target tissue. The term "distal" is used here to refer generally to the end or side of the filtration device or component thereof that is closer to the target tissue site than to the operator of the device.

In certain embodiments, the filtration device may be disposed within a catheter—e.g., with a filtering component disposed at the distal end of the catheter. The filtration device may include a frame structure coupled to one or more membranes having filtration material disposed thereon or contained between multiple membrane layers. In some instances, the filtration material may be disposed between multiple membranes without being attached to the membrane, such as a slurry disposed between multiple membranes. The catheter may be constructed in a variety of diameters that would fit the various sizes of blood vessels. For example, small vein diameters, such as renal or hepatic veins, may include, but are not limited to, diameters between approximately 8-14 mm; and large vein diameters, such as vena cava, may include, but are not limited to diameters between approximately 20-30 mm. The catheter would sheath, for example, the filtration device to enable endovascular delivery and retrieval of the filter device. A portion of the filtration device inside the sheath may include the framing structure and membranes such that the framing structure and membrane are displaced out the distal end of the sheath and concentrically or eccentrically open along the target blood vessel wall during positioning. In some instances, the membranes and the filtration material may be removable from the frame structure to enable the filtration device to be removed and exchanged as many times as needed through a lumen of the catheter (e.g., central lumen, or other lumen within the catheter).

In certain embodiments, the filtration material may be disposed on one or more porous membranes. For example, the filtration material may be disposed between two or more porous membranes.

The porosity of the membrane may vary but should be sufficient to enable blood to pass through. In one embodiment, the porosity of the membrane may be selected based on the therapeutic agent particle size—e.g., to capture therapeutic particles with a size larger than the pore size. Example pore sizes may include, but are not limited to pore sizes as small as 40 microns to as large as 300 microns. Other pore sizes may also be implemented.

In certain embodiments, the filtering component is positioned at the distal end of the filtration device. For example, the filtering component may include the membranes and filtration material. The filtering component may also include a frame structure that the one or more porous membranes are coupled thereto (e.g., adhered).

The frame structure may be expandable and constrainable to enable entry into the blood vessel when constrained and to occlude the blood vessel when expanded. For example, the frame structure may be biased to an expanded state when no outside force is applied, and constrained when an outside force is applied, such as being drawn within the catheter. The frame structure may have, for example, a wire mesh configuration that is constrainable when drawn within the catheter. The frame structure may be made from any variety of materials, such as, but not limited to, metals, metal alloys, polymeric materials, etc. For instance, in one embodiment, the material of the frame structure may include nitinol alloy. In some instances, the material of the frame structure may include platinum or other higher atomic number metal beads or markers attached for increased radiopacity to facilitate deployment and monitoring intraprocedurally. The frame structure, and the filtration device in general, may be constructed to be non-thrombogenic without significant binding or filtration of endogenous entities in the blood. In some instances, the frame structure may include a self-expanding configuration having interlocking joints, such as described in U.S. Pat. No. 5,800,517, the entirety of which is incorporated herein by reference.

In certain embodiments, the frame structure is concentrically or eccentrically positioned around the membrane and the filtration material. The filtration material may be disposed between the membrane and the outer frame structure for example. In other embodiments, multiple membranes may be coupled to the frame structure. The membrane may be flat in some instances, or folded or otherwise shaped to increase surface area in other instances.

In certain embodiments, the membrane is porous to permit blood to pass through and encounter the filtration material. The membrane may be made from a variety of materials but should enable blood to pass through. Example membrane materials may include, but are not limited to, fabrics, plastics, polymers, silicone, metals, metal alloys, etc. In certain embodiments, the membrane materials may themselves be composed of the filtration material that has properties to adsorb, bind, trap, inactivate or degrade the therapeutic agent. For instance, the membrane material may be impregnated with resin or carbon, or otherwise be composed of a resin or carbon. In certain embodiments, the membrane is sufficiently porous to permit the therapeutic agent to pass but filtered when contacting the filtration material.

The shape of the frame structure when expanded may vary, but should occupy most if not all of the cross section of the blood vessel. Having the frame structure expand to the entire cross section of the blood vessel may ensure the most amount of blood and therapeutic agent to enter the filtering component, and further may provide support or stability to retain the frame structure within the blood vessel. In some instances, the frame structure has a generally circular cross shape such as to conform to the generally circular cross shape of blood vessel. In some instances, the frame structure is tapered, or otherwise decreasing in cross sectional area, from the distal end towards the proximal end. This may, for example, facilitate blood flow through the filtering component while minimizing the amount of resistance to the flow of blood.

The filtration device shown may also include an elongated control member that extends within the lumen of the catheter and operably coupled to the frame structure. The elongated control member may, in some embodiments, enable an operator to displace the frame structure in and out of the distal end of the catheter to constrain and expand the frame structure, respectively. The elongated control member may also be used by an operator to position the filtration device to the target location within the blood vessel downstream from the target tissue site. In some instances, more than one elongated control member may be implemented.

In certain embodiments, the filtration device is positioned within a vein draining a target organ—e.g., an organ containing diseased or cancerous tissue—or a central vein. In some instances, for example, the filtration device may be inserted within an internal jugular or femoral vein. The filtration device may be dimensioned and sufficiently malleable to conform to walls of the vein, such as the renal vein, hepatic vein, vena cavae, or dural venous sinus.

In certain embodiments, the filtration device may include a removable and/or replaceable filtering component, or portion thereof. For example, the filtering component, or portion thereof, may be unique for any drug or variety of drug cocktails, both oncologic and non-oncologic, and removed and exchanged for another filtering component, or portion thereof, for the same or different drug or drug cocktail. For instance, stroke patients receiving thrombolytic drugs intraarterially could also greatly benefit from filtration of such drugs.

Figure 2A:
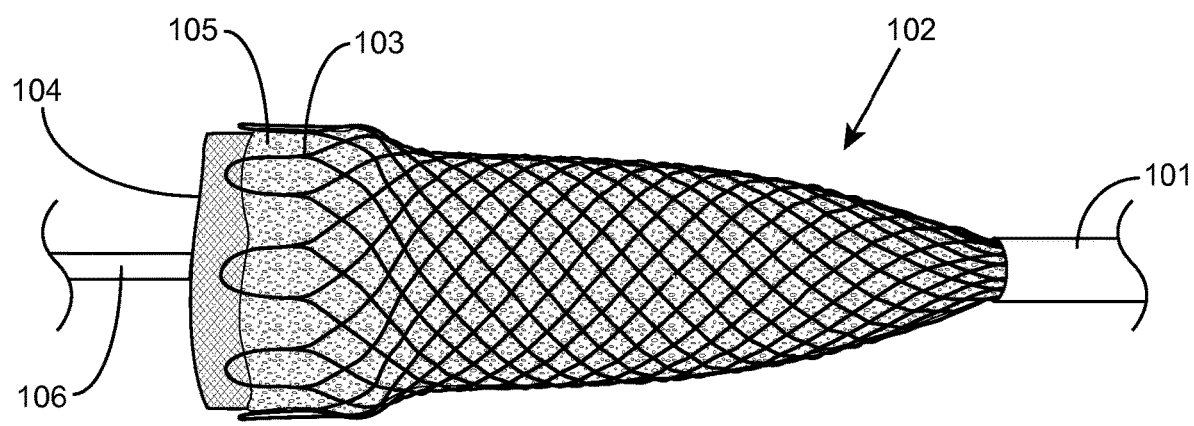
FIGS. 2A and 2B illustrate a close-up side view and a close-up top perspective view, respectively, of the filtration component shown in FIG. 1.
Figure 2B:
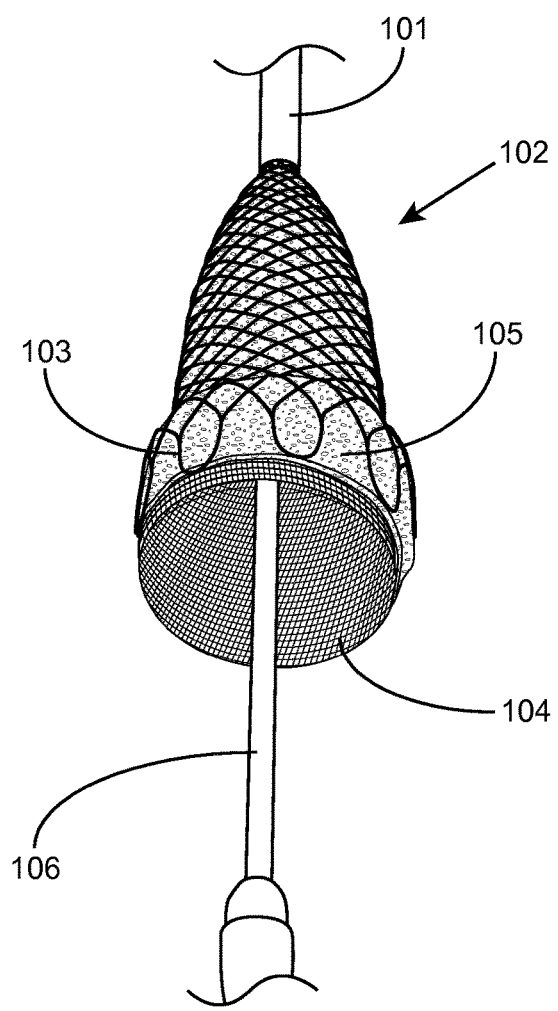

FIG. 1 illustrates an in vivo positionable filtration device for filtering a therapeutic agent in blood flowing in a blood vessel, according to one embodiment. Filtration device 100 includes catheter 101, filtering component 102 disposed at the distal end of the catheter 101, and handle 107 disposed at the proximal end of the catheter 101. The filtering component 102 includes a frame structure 103 coupled to a membrane 104 having filtration material 105 disposed thereon. FIGS. 2A and 2B illustrate a close-up side view and close-up top perspective view, respectively, of the filtering component 102 shown in FIG. 1, and are described in conjunction with FIG. 1.

The frame structure 103 may be expandable and constrainable to enable entry into the blood vessel when constrained and enable occlusion of the blood vessel when expanded. For example, the frame structure 103 may be biased to an expanded state when no outside force is applied, and constrained when an outside force is applied, such as being drawn within the catheter. The frame structure 103 may have, for example, a wire mesh configuration that is constrainable when drawn within the catheter 101. The frame structure 103 may be made from any variety of materials, such as, but not limited to, metals, metal alloys, polymeric materials, etc.

In the embodiment shown, the frame structure 103 is concentrically positioned around the membrane 104 and the filtration material 105. The filtration material 105 is disposed between the membrane 104 and the outer frame structure 103. In other embodiment, multiple membranes may be coupled to the frame structure. For example, multiple membranes may be positioned concentrically within the frame structure with the filtration material disposed between both membranes. It should be understood that other variations of the relative placement of the frame structure, membranes, and filtration material may be implemented in other embodiments. For example, in one embodiment, a membrane may be most interiorly positioned within the filtering component, and in another embodiment, the filtration material may be most interiorly positioned within the filtering component. In another embodiment, one or more membranes and the filtration material may be disposed concentrically around the frame structure.

In certain embodiments, the membrane 104 is porous to permit blood and therapeutic agent to pass through and encounter the filtration material. The membrane may be made from a variety of materials but should enable blood to pass. In certain embodiment, the membrane has a pore size that is larger than the therapeutic agent. In certain embodiments, the membrane has a pore size that is smaller than the therapeutic agent to prevent passage of the therapeutic agent past the filtering component. Example membrane materials may include, but are not limited to, fabrics, plastics, polymers, silicone, metals, metal alloys, etc. In certain embodiments, the membrane is made from a material with properties to adhere well to the filtration material.

It is appreciated that the frame structure may be porous and function as a membrane. In other embodiments, the filtration material may be disposed on a porous frame structure, such as mesh or scaffolding, without an additional membrane coupled to the frame structure.

The shape of the frame structure when expanded may vary, but should occupy most if not all of the cross section of the blood vessel. Having the frame structure expand to the entire cross section of the blood vessel may ensure the most amount of blood and therapeutic agent enter the receiving component, and further may provide support or stability to retain the frame structure within the blood vessel. In some instances, the frame structure has a generally circular cross shape such as to conform to the generally circular cross shape of blood vessel. In some instances, the frame structure is tapered, or otherwise decreasing in cross sectional area, from the distal end towards the proximal end—e.g., to facilitate blood flow through the filtering component while minimizing the amount of resistance to the flow of blood.

The filtration device shown in FIG. 1 also includes an elongated control member that extends within a lumen of the catheter and is operably coupled to the frame structure. The elongated control member enables an operator to displace the frame structure in and out of the distal end of the catheter to constrain and expand the frame structure, respectively. The elongated control member may also be used by an operator to position the filtration device to the target location within the blood vessel downstream from the target tissue site. In one embodiment, the elongated member 106 is removably coupled to the frame structure 103.

Figure 3:
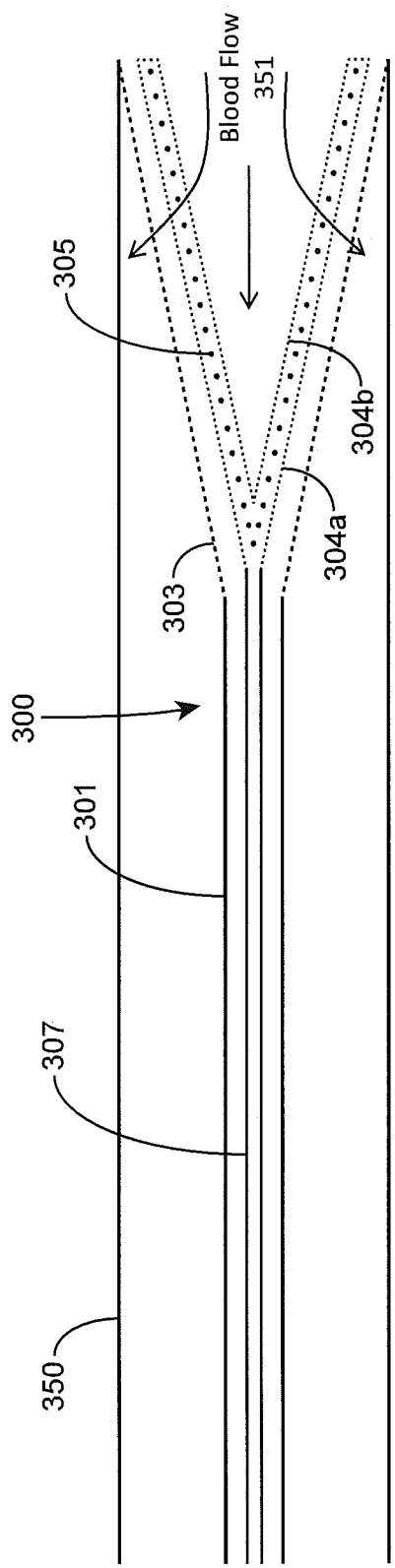

FIGS. 3-10 illustrate exemplary filtration devices according to different embodiments. FIG. 3 illustrates an example filtration device, according to one embodiment. Filtration device 300 includes an elongated control member 307 that is operably coupled to a frame structure 303. Frame structure 303 is coupled to two porous membranes 304a,304b that have filtration material 305 disposed between the two porous membranes 304a,304b. In another embodiment, a single porous membrane composed of the filtration material 305 is disposed within the frame structure 303.

The elongated control member 307 is operably coupled to the frame structure 303 and is used to displace the frame structure 305, porous membranes 304a,304b, and filtration material 305 horizontally along the central axis of the catheter 301. The frame structure 303 is biased to an expanded state so that when the frame structure 303 is displaced outside the distal end of the catheter 301, as shown, the frame structure 303 is expanded to occupy the cross sectional area of the blood vessel 350. For example, x-ray fluoroscopy may be used to confirm the tip. The frame structure 303 is constrainable such that when the frame structure 303 is drawn within the distal end of catheter 301, the frame structure 303 constrains to fit within the catheter 301 along with the porous membranes 304a,304b, and filtration material 305.

In the embodiment shown, the filtering component includes a porous frame structure 303 (e.g., mesh), the two porous membranes 304a,304b, and filtration material 305. When the frame structure 303 is expanded, the filtering component is conical shaped or otherwise tapered. After the blood 351 and therapeutic agent (e.g., non-chemotherapeutic agent or chemotherapeutic agent, such as Dox) are administered upstream from a target tissue site and eventually contact with the target tissue site, the blood 351 and therapeutic agent then flow into the distal end of the filtering component and contact the porous membranes 304a,304b and filtration material 305. The blood 351 passes through the porous frame structure 303 (e.g., mesh), two porous membranes 304a,304b, and filtration material 305, while the therapeutic agent is filtered by the filtration material 305.

It should be appreciated that the frame structure 303 may be part of the catheter 101 or independently positioned within catheter 101. Furthermore, the elongated control member 307, membranes 304a,304b and filtration material 305 may be part of the frame structure 303 or removably coupled to the frame structure, or independently positioned within the catheter 101 and frame structure 303. In this way, the elongated member 307, membranes 304a,304b, and filtration material 305 may be introduced within catheter 301 and frame structure 303 and thereafter removed (e.g., for continuous replacement during the procedure) while the catheter 301 and/or frame structure 303 remains positioned within the blood vessel. It should be appreciated that this may also be applicable to the other example embodiments shown in the figures.

Figure 4:
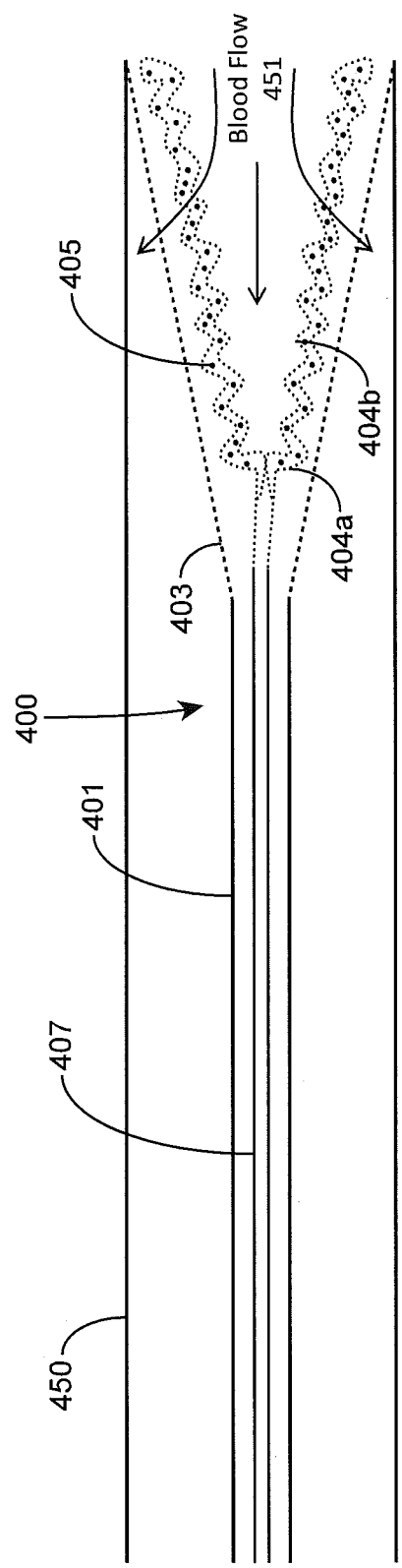

FIG. 4 illustrates an example filtration device, according to one embodiment. Filtration device 400 includes an elongated control member 407 that is operably coupled to a frame structure 403. Frame structure 403 is coupled to two porous membranes 404a,404b that have filtration material 405 disposed between the two porous membranes 404a, 404b.

The elongated control member 407 is operably coupled to the frame structure 403 and is used to displace the frame structure 405, porous membranes 404a,404b, and filtration material 405 horizontally along the central axis of the catheter 401. The frame structure 403 is biased to an expanded state so that when the frame structure 403 is displaced outside the distal end of the catheter 401, as shown, the frame structure 403 is expanded to occupy the cross sectional area of the blood vessel 450. The frame structure 403 is constrainable such that when the frame structure 403 is drawn within the distal end of catheter 401, the frame structure 403 constrains to fit within the catheter 401 along with the porous membranes 404a,404b, and filtration material 405.

In the embodiment shown, the filtering component includes a porous frame structure 403 (e.g., mesh), the two porous membranes 404a,404b, and filtration material 405. The membranes 404a,404b are folded or otherwise shaped in an uneven manner to increase the surface area of the membranes 404a,404b that contacts the blood 451 and therapeutic agent. When the frame structure 403 is expanded, the filtering component is conical shaped or otherwise tapered. After the blood and therapeutic agent (e.g., non-chemotherapeutic agent or chemotherapeutic agent, such as Dox) are administered upstream from a target tissue site and eventually contact with the target tissue site, the blood 451 and therapeutic agent then flow into the distal end of the filtering component and contact the porous membranes 404a,404b and filtration material 405. The blood 451 passes through the porous frame structure 403 (e.g., mesh), two porous membranes 404a,404b, and filtration material 405, while the therapeutic agent is filtered by the filtration material 405.

FIG. 5 illustrates an example filtration device, according to one embodiment. Filtration device 500 includes an elongated control member 507 that is operably coupled to a frame structure 503. Frame structure 503 is coupled to two porous membranes 504a,504b. Instead of having filtration material disposed between the two membranes 504a,504b, the membranes 504a,504b are composed of a filtration material that filters the therapeutic agent. For example, membranes 504a,504b may be composed of resin or carbon material, or may be made from a material that is impregnated with a filtration material having adsorptive, binding, or catalytic properties. In another embodiment, a single membrane composed of the filtration material is disposed on the frame structure 503.

The elongated control member 507 is operably coupled to the frame structure 503 and is used to displace the frame structure 505 and porous membranes 504a,504b horizontally along the central axis of the catheter 501. The frame structure 503 is biased to an expanded state so that when the frame structure 503 is displaced outside the distal end of the catheter 501, as shown, the frame structure 503 is expanded to occupy the cross sectional area of the blood vessel 550. The frame structure 503 is constrainable such that when the frame structure 503 is drawn within the distal end of catheter 501, the frame structure 503 constrains to fit within the catheter 501 along with the porous membranes 504a,504b containing the filtration material.

In the embodiment shown, the filtering component includes the porous frame structure 503 (e.g., mesh) and the two porous membranes 504a,504b composed of the filtration material. When the frame structure 503 is expanded, the filtering component is conical shaped or otherwise tapered. After the blood 551 and therapeutic agent (e.g., non-chemotherapeutic agent or chemotherapeutic agent such as Dox) are administered upstream from a target tissue site and eventually contact with the target tissue site, the blood 551 and therapeutic agent then flow into the distal end of the filtering component and contact the porous membranes 504a,504b composed of the filtration material. The blood 551 passes through the porous frame structure 503 (e.g., mesh) and two porous membranes 504a,504b composed of the filtration material, while the therapeutic agent is filtered by the membranes 504a,504b composed of the filtration material.

FIG. 6 illustrates an example filtration device, according to one embodiment. Filtration device 600 includes an elongated control member 607 that is operably coupled to a frame structure 603. Frame structure 603 is coupled to a structure of filtration elements 604 made of a filtration material that filters the therapeutic agent. The structure of elements 604 may have any variety of shapes, sizes, and densities. For example, each of the filtration elements of the structure 604 may be linear members (e.g., resembling bristles on a brushes), non-linear members, sheets or membranes, etc. The structure of filtration elements 604 may, for example, be composed of a filtration material having adsorptive, binding, or catalytic properties (e.g., resin, carbon, catalytic material, etc.), or may be made from a material that is impregnated with a filtration material (e.g., particles) having such adsorptive, binding, or catalytic properties.

The structure of filtration elements 604 may have any variety of three dimensionally shaped configurations that provide increased filtering as blood and therapeutic agents enter further into the structure of elements 604. The structure may include varying patterns (e.g., regular or irregular patterns), sizes and thicknesses In certain embodiments, the structure 604 may be constructed of one or more thick layers of porous membrane, or multiple densely packed filtration elements (e.g., linear members, porous membranes, etc.) to resemble a sponge-like structure.

In another embodiment, the structure 604 may be constructed with filtration elements extending from a central axis member 608 to the frame structure 603. In some instances, the central axis member 608 is the elongated control member 607 or extension therefrom. The pattern of the filtration elements 604 may vary, and may include any regular or irregular patterns. For instance, in one embodiment, the porous membranes extend radially outward from the central axis member 608 towards the frame structure 608 to resemble a pipe-brush configuration. In yet another embodiment, the structure 604 may be constructed with tiny resin beads being attached together (e.g., in a linear array connected with a thin wire). That string would have high surface area and could be introduced and removed easily.

The elongated control member 607 is operably coupled to the frame structure 603 and is used to displace the frame structure 605 and the structure of filtration elements 604 horizontally along the central axis of the catheter 601. The frame structure 603 is biased to an expanded state so that when the frame structure 603 is displaced outside the distal end of the catheter 601, as shown, the frame structure 603 is expanded to occupy the cross sectional area of the blood vessel 650. The frame structure 603 is constrainable such that when the frame structure 603 is drawn within the distal end of catheter 601, the frame structure 603 constrains to fit within the catheter 601 along with the structure of filtration elements 604 composed of a filtration material.

In the embodiment shown, the filtering component includes the porous frame structure 603 (e.g., mesh) and the structure of filtration elements 604 containing the filtration material. When the frame structure 603 is expanded, the frame structure 603 is conical shaped or otherwise tapered. After the blood 651 and therapeutic agent (e.g., non-chemotherapeutic agent or chemotherapeutic agent such as Dox) are administered upstream from a target tissue site and eventually contact with the target tissue site, the blood and therapeutic agent then flow into the distal end of the filtering component and contact the structure of filtration elements 604 composed of the filtration material. The blood 651 passes through the porous frame structure 503 (e.g., mesh) and structure of filtration elements 604 composed of the filtration material, while the therapeutic agent is filtered by the structure of filtration elements 604 composed of the filtration material.

Figure 7:
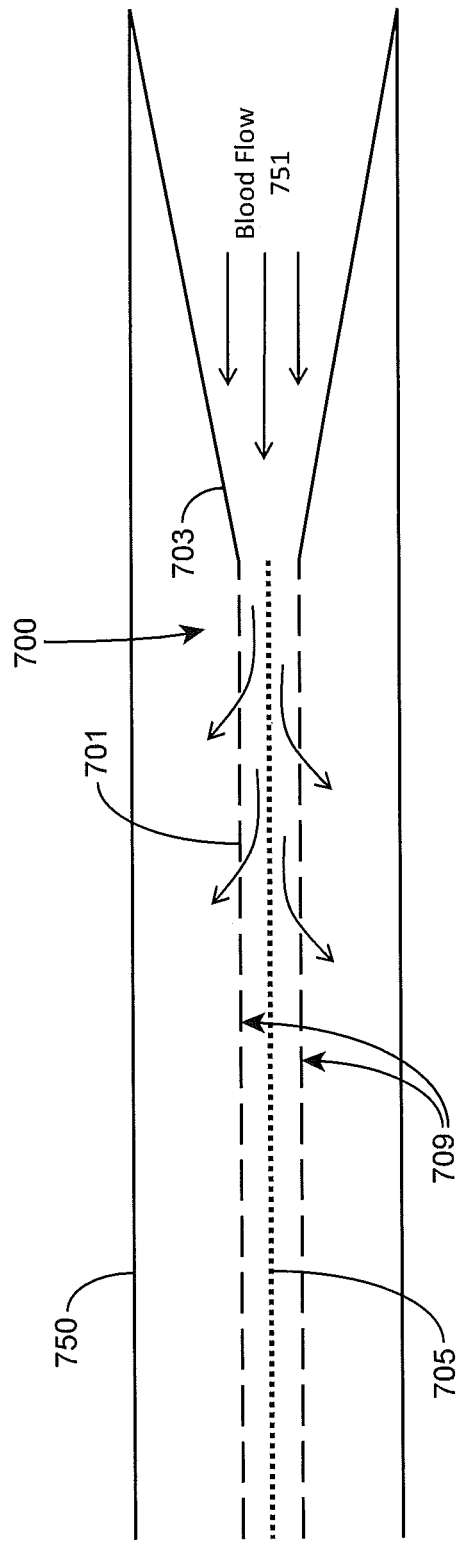

FIG. 7 illustrates an example filtration device, according to one embodiment. Filtration device 700 includes an elongated control member (not shown) that is operably coupled to a frame structure 703. The elongated control member is operably coupled to the frame structure 703 and is used to displace the frame structure 705 horizontally along the central axis of the catheter 701. The frame structure 703 is biased to an expanded state so that when the frame structure 703 is displaced outside the distal end of the catheter 701, as shown, the frame structure 703 is expanded to occupy the cross sectional area of the blood vessel 750. The frame structure 703 is constrainable such that when the frame structure 703 is drawn within the distal end of catheter 701, the frame structure 703 constrains to fit within the catheter 701.

Instead of having filtration material disposed on the frame structure 703, the filtration material 705 is disposed within a lumen of the catheter 701. For example, in one embodiment, the filtration material may be pre-packed within the lumen of the catheter 701. In some instances, the filtration material may be removable and replaceable, such as by a wire attached to the filtration material or by removing or replacing a pre-packed filtration cartridge that fits within the lumen of the catheter. In one embodiment, filtration material 705 may be disposed on the elongated control member extending along the central axis of the catheter 701. In some instances, the filtration material 705 may be removable and replaceable by the elongated control member. In another embodiment, the filtration material may be disposed around the elongated control member. In certain embodiments, the filtration material includes resin or carbon material, or other filtration material having adsorptive, binding, or catalytic properties.

The catheter 701 includes holes 709 that permit the blood to pass through from the lumen of the catheter 701 to the blood vessel 750. In some instances, the holes 709 may be sized to be smaller than the size of the particles of the filtration material. For example, the filtration material may include beads having properties that absorb, bind, or inactivate or degrade the therapeutic agent, and the holes sized smaller than the size of the beads.

In the embodiment shown, the filtering component includes filtration material 705 and holes 709. When the non-porous frame structure 703 is expanded, the frame structure 703 is conical shaped or otherwise tapered to direct blood 751 and therapeutic agent into the lumen of the catheter 701. After the blood and therapeutic agent (e.g., non-chemotherapeutic agent or chemotherapeutic agent such as Dox) are administered upstream from a target tissue site and eventually contact with the target tissue site, the blood and therapeutic agent then flow into the distal end of the frame structure 703 and directed to the lumen of the catheter 701 to come into contact with the filtration material 705 disposed within the lumen of the catheter. The blood 751 passes by or through the filtration material 705 and out the holes 709 of the catheter 701, while the therapeutic agent is filtered by the filtration material 705.

Figure 8:
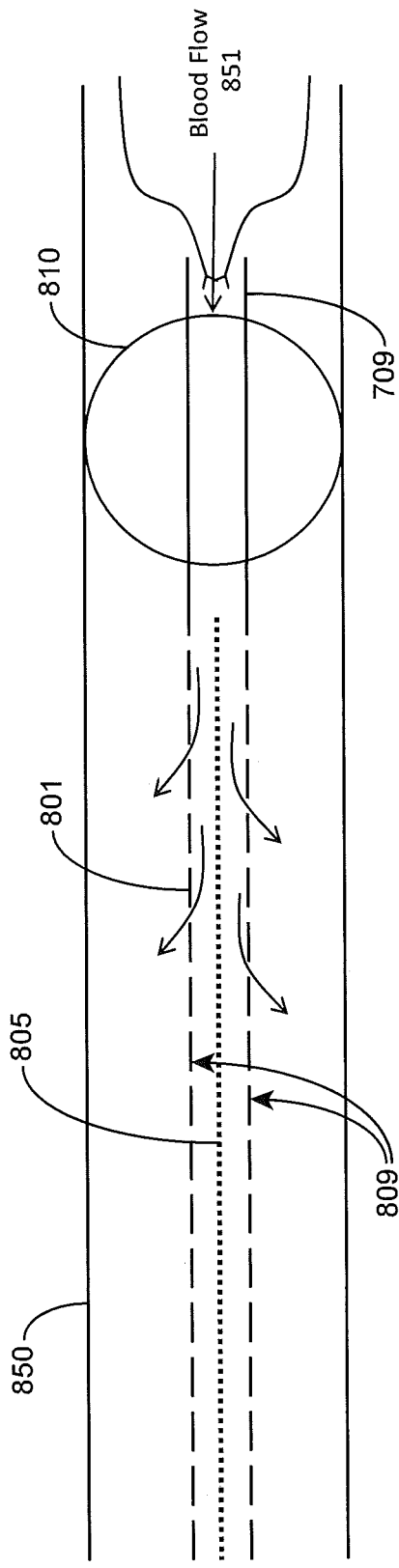

FIG. 8 illustrates an example filtration device, according to one embodiment. Filtration device 800 includes an inflatable balloon 810 that is disposed on frame structure 803 at the distal end of the catheter 801. In the embodiment shown, the frame structure 803 is the distal portion of the catheter 801. In another embodiment, the frame structure 803 may be a separate element coupled to the catheter 801.

The inflatable balloon 810 is disposed at the distal end of catheter 801 and may be deflated when the filtration device is being positioned within the blood vessel, and then inflated when positioned at the target site downstream from the target tissue. The term "balloon" is used broadly herein to refer to any type of chamber, container, etc., that can fill with air or fluid and expand.

When inflated, the balloon 810 occupies the cross sectional area of the blood vessel 850 to obstruct the blood flow in blood vessel and direct it into the distal end of the lumen of the catheter 801.

Filtration material 805 is disposed within the lumen of the catheter 801, as similarly described for FIG. 7. For example, the filtration material 805 may be disposed on or around an elongated control member extending along the central axis of the catheter 801. The elongated control member may be used, for example, to position the inflatable balloon 810 and to add or remove air or fluid to inflate or deflate the balloon 810, respectively. In certain embodiments, the filtration material 805 includes resin or carbon material, or other filtration material having adsorptive, binding, or catalytic properties.

The catheter 801 includes holes 809 that permit the blood to pass through from the lumen of the catheter 801 to the blood vessel 850, as similarly described for FIG. 7. In the embodiment shown, when the inflatable balloon 810 is inflated, the balloon 810 occupies the cross sectional area of the blood vessel 850 to obstruct the blood flow in blood vessel and direct it into the distal end of the lumen of the catheter 801.

In the embodiment shown, the filtering component includes filtration material 805 and holes 809. After the blood 851 and therapeutic agent (e.g., non-chemotherapeutic agent or chemotherapeutic agent such as Dox) are administered upstream from a target tissue site and eventually contact with the target tissue site, the blood and therapeutic agent are then obstructed by the inflatable balloon 810 and directed into the distal end of the lumen of the catheter 801 and directed to the lumen of the catheter 801 to come into contact with the filtration material 805 disposed within the lumen of the catheter 801. The blood 851 passes by or through the filtration material 805 and out the holes 809 of the catheter 801, while the therapeutic agent is filtered by the filtration material 805.

FIG. 9 illustrates an example filtration device, according to one embodiment. Filtration device 900 includes an elongated control member 907 that is operably coupled to porous membranes 904a,904b, also functioning as the frame structure in this embodiments. Membranes 904a,904b have filtration material 905 disposed between the two porous membranes 904a,904b.

The elongated control member 907 is operably coupled to the porous membranes 904a,904b and is used to displace the porous membranes 904a,904b and filtration material 905 horizontally along the central axis of the catheter 301. The porous membranes 904a,904b are biased to an expanded state so that when the porous membranes 904a,904b are displaced outside the distal end of the catheter 901, as shown, the porous membranes 904a,904b are expanded to occupy the cross sectional area of the blood vessel 950. In the embodiment shown, the porous membranes 904a,904b are shaped to direct blood flow away from the radial center of the vessel—e.g., conically shaped to decrease in cross sectional size towards the distal end. The widest cross section area of membranes 904a,904b at the proximal end of the membranes 904a,904b occupies the cross sectional area of the blood vessel 950 when the membranes 904a,904b are expanded.

The membranes 904a,904b are constrainable such that when the membranes 904a,904b is drawn within the distal end of catheter 901 via the elongated control member 907, the membranes 904a,904b constrains to fit within the catheter 301 along with the filtration material 905. The term "constrain" is used broadly herein and may include constricting, contracting, compressing, bending, or otherwise altering the material or element to become narrower, such as to fit within the lumen of the catheter when constrained and to expand in size to occupy the blood vessel when outside the catheter. In the embodiment shown, the elongated control member 907 may be used to pull the membranes 904a,904b back into the distal end of the catheter 901 by bending and compressing the conical membranes 904a,904b as it is drawn into the catheter 901, for example.

In the embodiment shown, the filtering component includes membranes 904a,904b and filtration material 905. When the membranes 904a,904b are expanded, the membranes 904a,904b are conical shaped to direct blood flow away from the radial center of the vessel. After the blood and therapeutic agent (e.g., non-chemotherapeutic agent or chemotherapeutic agent, such as Dox) are administered upstream from a target tissue site and eventually contact with the target tissue site, the blood 951 and therapeutic agent then flow to the distal end of the filtering component and contact the porous membranes 904a,904b and filtration material 905. The blood 951 is directed away from the radial center of the blood vessel, eventually passing through the porous membranes 904a,904b and filtration material 905, while the therapeutic agent is filtered by the filtration material 305.

FIG. 10 illustrates an example filtration device, according to one embodiment. Filtration device 1000 includes an elongated control member 1007 that is operably coupled to porous membranes 1004a,1004b, also functioning as the frame structure in this embodiments. Membranes 1004a, 1004b have filtration material 1005 disposed between the two porous membranes 1004a,1004b.

The elongated control member 1007 is operably coupled to the porous membranes 1004a,1004b and is used to displace the porous membranes 1004a,1004b and filtration material 1005 horizontally along the central axis of the catheter 1001. The porous membranes 1004a,1004b are biased to an expanded state so that when the porous membranes 1004a,1004b are displaced outside the distal end of the catheter 1001, as shown, the porous membranes 1004a, 1004b are expanded to occupy the cross sectional area of the blood vessel 1050. In the embodiment shown, the porous membranes 1004a,1004b are shaped to increase and then decrease in cross-sectional area from the distal end towards the proximal end. At the widest cross sectional area of membranes 1004a,1004b, the membranes 1004a,1004b occupies the cross sectional area of the blood vessel 1050 when the membranes 1004a,1004b are expanded.

The membranes 1004a,1004b are constrainable such that when the membranes 1004a,1004b are drawn within the distal end of catheter 1001 via the elongated control member 1007, the membranes 1004a,1004b constrains to fit within the catheter 1001 along with the filtration material 1005. In the embodiment shown, the elongated control member 1007 may be used to pull the membranes 1004a,1004b back into the distal end of the catheter 1001 by constraining the conical membranes 1004a,1004b as it is drawn into the catheter 1001, for example.

In the embodiment shown, the filtering component includes membranes 1004a,1004b and filtration material 1005. When the membranes 1004a,1004b are expanded, the distal side of membranes 1004a,1004b are conical shaped to direct blood flow away from the radial center of the vessel. After the blood and therapeutic agent (e.g., non-chemotherapeutic agent or chemotherapeutic agent, such as Dox) are administered upstream from a target tissue site and eventually contact with the target tissue site, the blood and therapeutic agent then flow to the distal end of the filtering component and contact the porous membranes 1004a,1004b and filtration material 1005. The blood 1051 is directed away from the radial center of the blood vessel, eventually passing through the distal side of the porous membranes 1004a,1004b and filtration material 1005, and then again passing through the proximal side of the porous membranes 1004a,1004b and filtration material 1005, which tapers towards the radial center of the blood vessel. Similarly, the therapeutic agent is filtered by the filtration material 1005 as it passes contacts the distal side of the porous membranes 1004a,1004b and filtration material 1005. Any therapeutic agent that passes through the distal side of the porous membranes 1004a,1004b without being filtered by the filtration material 1005, will then contact the proximal side of the porous membranes 1004a,1004b and filtered by the filtration material 1005.

The filtration devices shown in FIGS. 3-10 are exemplary and may vary in configuration in other embodiments, such as to include features described in other parts of the present disclosure. In certain embodiments, the filtration material may include one or more types of material having properties that adsorb, bind, or inactivate or degrade one or more therapeutic agents, and each may be either non-chemotherapeutic or chemotherapeutic, independent of the other. In certain embodiment, the filtration material adsorbs and/or chemically binds to the therapeutic agent. For example, the filtration material may include a resin or activated carbon having properties to adsorb and/or chemically bind to the therapeutic agent, and/or magnetically bind to a magnetic carrier bound to the therapeutic agent. The therapeutic agent may include doxorubicin, for example, and the filtration material may include, but is not limited to: strong acid cation exchange polymer resins; ion exchange resins; polymeric adsorbent resins without ion exchange; resins including sulfonate groups that ionically bond to the therapeutic agent; chromatography based resins, or any combination thereof. In certain embodiments, the filtration material may include a material that inactivates or degrades the therapeutic agent. For example, the filtration material may include a catalytic material that enzymatically degrades a therapeutic agent, such as Dox. In one embodiment, the filtration material may include a material that adsorb and/or chemically bind to the therapeutic agent and that inactivates or degrades the therapeutic agent. In certain embodiments, the filtration material may include a material that improves biocompatibility, such as polymethyl-methacrylate (PMMA), chitosan, heparin, etc. In some instances, for example, the resin or carbon may be coated or otherwise impregnated with the PMMA, chitosan, and/or heparin. Furthermore, as explained in other parts of the present disclosure, in some instances, the catheter may be integrated with the filtration device. In other instances, the filtration device may be removable and replaceable during use, such as with the catheter is still within the blood vessel. In some instances, the catheter includes the filtration device within its lumen when the catheter is being positioned in the blood vessel. In other instances, the filtration device may be inserted into the lumen of the catheter after the catheter is positioned in the blood vessel.

Methods

In some aspects of the present disclosure, methods of in vivo filtration of one or more therapeutic agents are provided. The methods include positioning a filtration device in a blood vessel of a body of a human or non-human animal, and administering a therapeutic agent upstream from the target tissue site to direct flow of the therapeutic agent to the target tissue site and then to the filtration device. The filtration device is positioned downstream from a target tissue site. Further, the filtration device is for filtering the therapeutic agent in the blood flowing in the blood vessel. The in vivo positioned filtration device filters the therapeutic agent as the blood and the therapeutic agent are received by the filtration device. Various examples of positioned devices in different blood vessels are depicted in FIGS. 14A-14J, including the hepatic vein (FIGS. 14A-14B), iliac vein (FIGS. 14C-14D), inferior vena cava (FIG. 14E), renal vein (FIGS. 14F-14G), and superior vena cava (FIGS. 14H-14L). Additional exempleory positioning of the present device also include, but are not limited to, intracranially in the dural venous sinuses (e.g., sigmoid sinus, transverse sinus, torcula, straight sinus, superior sagittal sinus) to remove agents during cerebral embolization or chemoinfusion; internal jugular vein with the device inserted, for example, either transfemorally or directly in the ipsilateral internal jugular vein, for head and neck tumors and during cerebral embolization or chemoinfusions; and the brachiocephalic vein between the superior vena cava and the internal jugular vein.

It should be appreciated that the methods may include the filtration devices described in the present disclosure, and for the sake of clarity and brevity, will not be described in great detail again, but rather reference is made to the previous discussion of these features. Additionally, the description of the methods of using the filtration devices is also applicable to the methods section, and will not be described again great detail again but rather reference is made to the previous discussion.

The target tissue may include, for example, cancerous or otherwise diseased tissue. The target tissue site should be accessible by the bloodstream and may include organs for instance. Example cancerous tissue sites may include, but are not limited to the liver, kidney, brain, head/neck, skin gastrointestinal tract, and musculoskeletal system. For example, the target tissue site may include an organ afflicted with cancerous growths.

The therapeutic agent is administered upstream from the target tissue site—e.g., intraarterially or intravenously supplying a cancerous or otherwise diseased organ. In certain embodiments, the filtration device is positioned within a vein draining a target organ—e.g., an organ containing diseased or cancerous tissue—or a central vein. In some instances, for example, the filtration device may be inserted within an internal jugular or femoral vein. In some instances, the filtration device may be malleable to conform to the vein, such as the renal vein, hepatic vein, or vena cavae.

The distance the filtration device is positioned from the target tissue site may vary based on the particular blood vessel, the location of the target tissue site (e.g., which organ), etc. The distance to the target tissue site or organ including the target tissue may vary. For instance, example distances may include, but are not limited to, distances from two feet or less, such as 6 inches or less, including three inches or less. In one embodiment, the distance may be less than one inch from the target tissue site or organ including the target tissue. In other embodiments, the distance to the target tissue site or organ may be greater than two feet, such as up to four feet—e.g., if for instance, a tumor was present in person's extremity such as a toe and the filtration device placed in the inferior vena cava. It should be appreciated that the ranges are exemplary, and distances outside the example ranges provided are also possible.

In certain embodiments, the filtration device may be positioned in the blood vessel by inserting a catheter within the blood vessel downstream from the target tissue. In one embodiment, the filtration device is positioned within the catheter at the time the catheter is inserted within the blood vessel. In another embodiment, the catheter is first inserted within the blood vessel, and thereafter the filtration device is inserted within the lumen of the catheter. When inside the catheter, an elongated control member may be used by the operator to displace the filtration device within the lumen of the catheter until a portion of the filtration device is displaced out the distal end of the catheter and into the blood vessel. The filtration device may include a frame structure that expands to occupy the entire cross sectional area of the blood vessel when the frame structure is displaced out the distal end of the catheter. The elongated control member may also be used by the operator to retract and constrain the exposed portion of the filtration device back inside the catheter.

In certain embodiments, the filtration device is removable from the catheter during use—e.g., while the catheter is still positioned inside the blood vessel. In some instances, the filtration device may be sterilized and reusable. In other instances, the filtration device may be disposable and a replacement filtration device may be inserted into the catheter after the original filtration device is discarded. The replacement filtration device is then displaced within the catheter until a portion of the replacement filtration device is displaced out the distal end of the catheter, and the filtration process repeated with the replacement filtration device.

It should be appreciated that the frame structure may be part of the catheter or independently positioned within catheter. Furthermore, the elongated control member, membranes, and filtration material, may be part of the frame structure or removably coupled to the frame structure, or independently positioned within the catheter and frame structure. In this way, the elongated member, membranes, and filtration material may be introduced within catheter and frame structure and thereafter removed (e.g., for continuous replacement during the procedure) while the catheter and/or frame structure remains positioned within the blood vessel.

After the filtering of the therapeutic agent is complete, the catheter may be removed from the blood vessel. In one embodiment, the filtration device is removed before the catheter. In another embodiment, the catheter is removed from the blood vessel while the filtration device is within the catheter. It should also be appreciated that in certain embodiments, the filter component is left within the blood vessel while the catheter is removed from the blood vessel. At a later time (e.g., days, weeks, months, etc.) the filter may be removed—e.g., with a snare catheter for instance. It is also appreciated that filters may be used and/or replaced during the procedure, with a filter remaining in the blood vessel after the procedure for removal at a later time.

The therapeutic agent may include, for example, any variety of agents, such as drugs or chemical substances used in the treatment, cure, prevention, or diagnosis of disease or used to otherwise enhance physical or mental well-being. The therapeutic agent may include, for example, chemotherapeutic agents and/or non-chemotherapeutic agents. In one embodiment, the therapeutic agent is Dox and used to treat cancerous tissue, such as within an organ. Non-chemotherapeutic agents may include, but are not limited to, for example, anti-coagulants, thrombolytics, etc. The thrombolytic may be used, for example, in stroke treatment.

It will be appreciated that in certain embodiments, the therapeutic gent administered to the subject is known to be therapeutically beneficial above a certain concentration level in the blood. After a certain time once the concentration decreases below a specific threshold, it is only primarily toxicity that the patient receives. In such embodiments, the present device may be placed intraarterially or intravenously at the time when the concentration drops below that agent's therapeutic level in order to filter the agent and prevent toxicity. It will be appreciated buy one of skill in the art that this timing may be derivable from published known in vivo kinetics/clearance profile of the therapeutic agent.

Example

Figure 11:
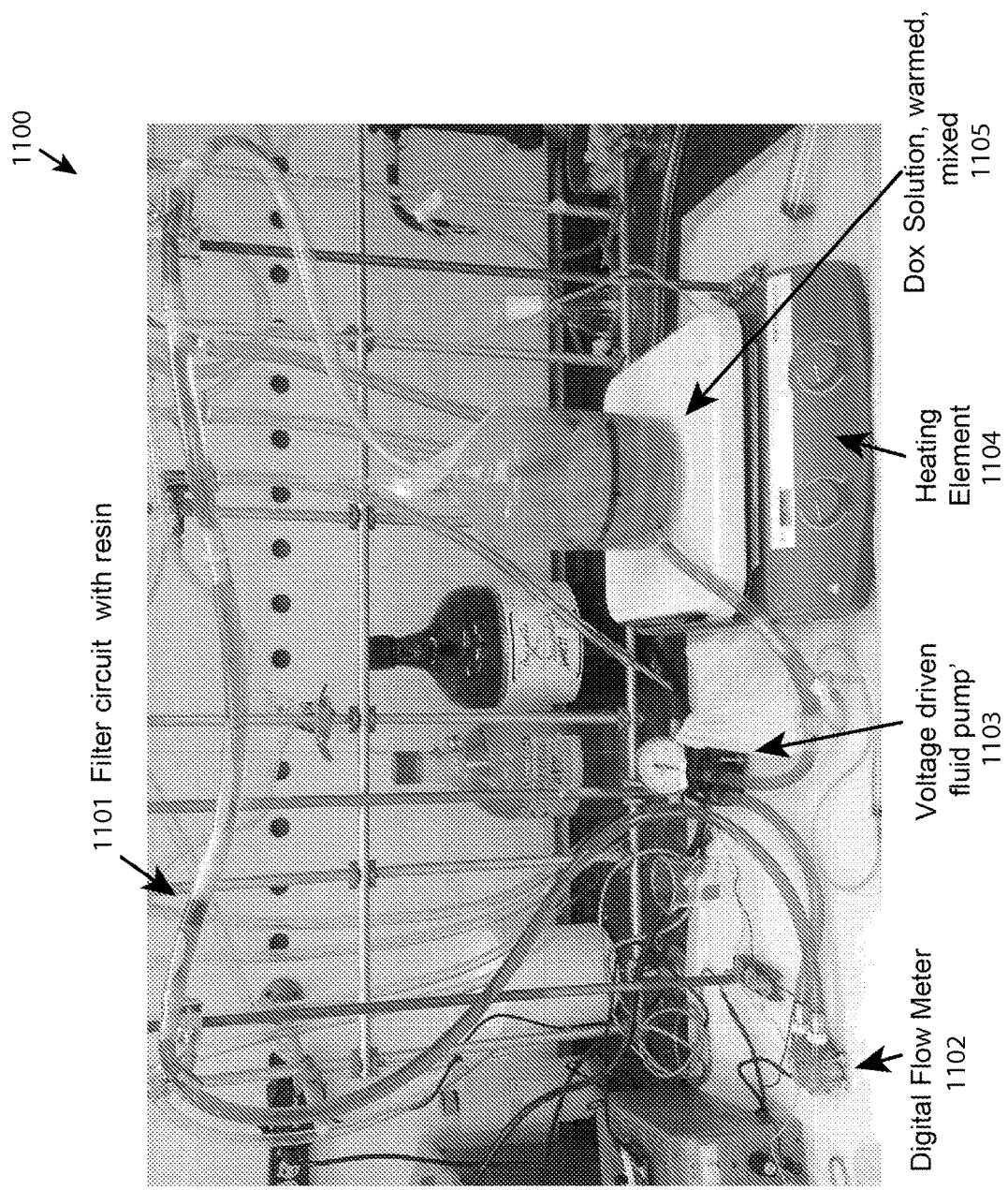
FIG. 11 illustrates an experimental model implementing a resin filter and Doxorubicin as a therapeutic agent, according to one embodiment.

FIG. 11 shows an in-vitro experimental flow model used to test the efficacy of various carbons and resins. Flow model 1100 is shown including a filter circuit with resin 1101, digital flow meter 1102, voltage drive fluid pump 1103, and container containing Dox solution 1105 coupled to one another via polymer tubing. The container of Dox solution 1105 is heated by heating element 1104.

The designed flow model simulates intraarterial chemotherapy delivery by employing a voltage governed fluid pump 1103 and digital flow meter 1102, which can control flow rate to match the renal vein (~750 ml/min). The dimensions of the polymer tubing used also matched that of an average renal vein, with filter segment measuring 6 cm in length and 1.2 cm in diameter (34). A 1 liter solution of phosphate buffered solution (PBS) with Ca2+ and Mg2+ is warmed and mixed to 37° C., thereby simulating a physiologic environment with serum electrolytes, pH, and temperature. A solution of concentrated 2 mg/ml Dox HCl is introduced into the system via injection ports to bring the overall solution Dox concentration to approximately 0.05 mg/ml (50 mg total drug, similar to a dose administered in transarterial chemoembolization (TACE). The filter column is filled with adsorbent material to a volume matching that of a cone in the renal vein (2.26 ml). The adsorbent materials are contained in the filter circuit by a 200-micron mesh filter (particles are greater than this size). A 200 micron size was selected since prior studies of carotid protection devices demonstrate this pore size to allow free passage of blood products with minimal pressure drops (35). Samples were taken from the flow model system for the next 1-4 hours, and Dox concentrations measured via UV spectrophotometry at its known peak wavelength of 480 nm.

Figure 12:
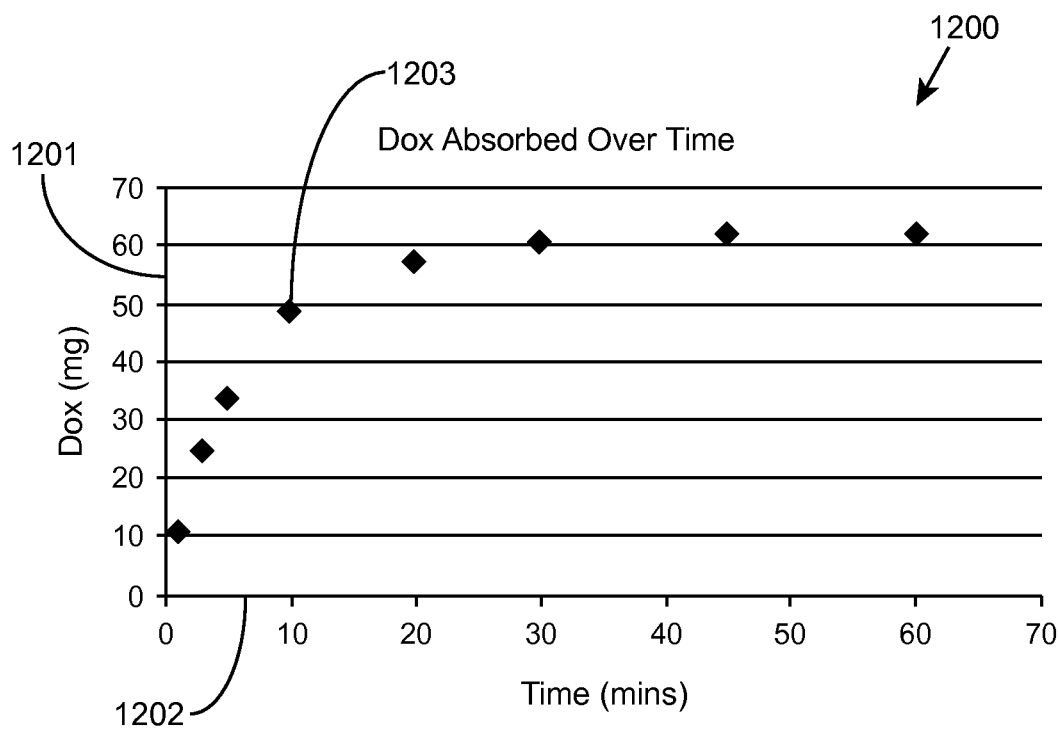
FIG. 12 illustrates a graph of Doxorubicin kinetic curve for a resin resulting from experimental data obtained with the experimental model shown in FIG. 11, according to one embodiment.
Figure 13:
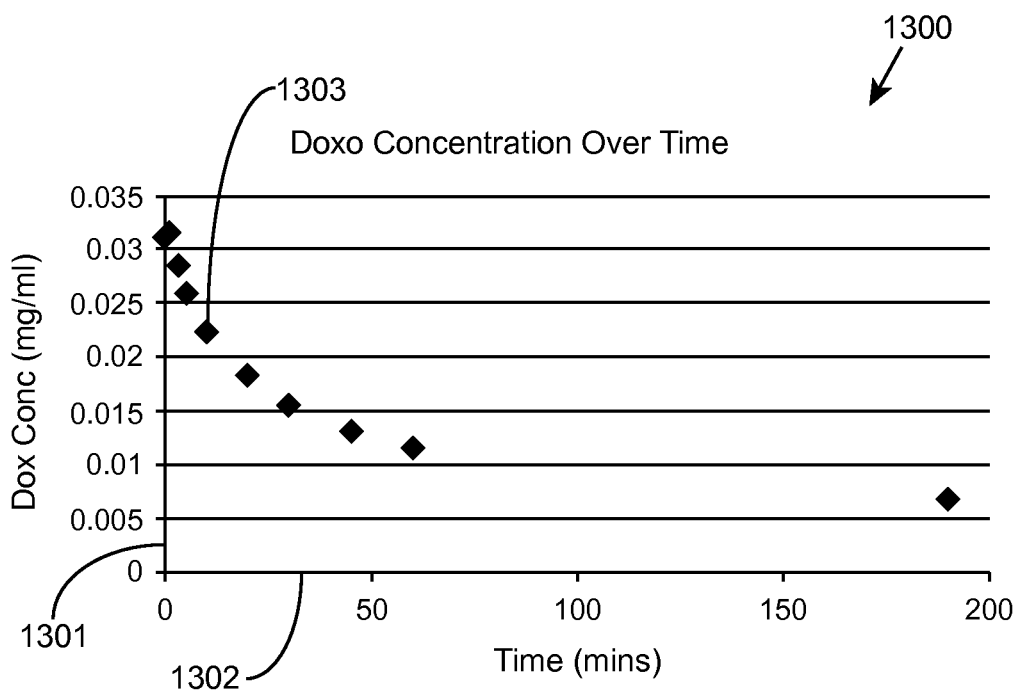
FIG. 13 illustrates a graph of Doxorubicin kinetic curve for adsorbent resin resulting from experimental data obtained with the experimental model shown in FIG. 11, according to one embodiment.
Figure 14A:
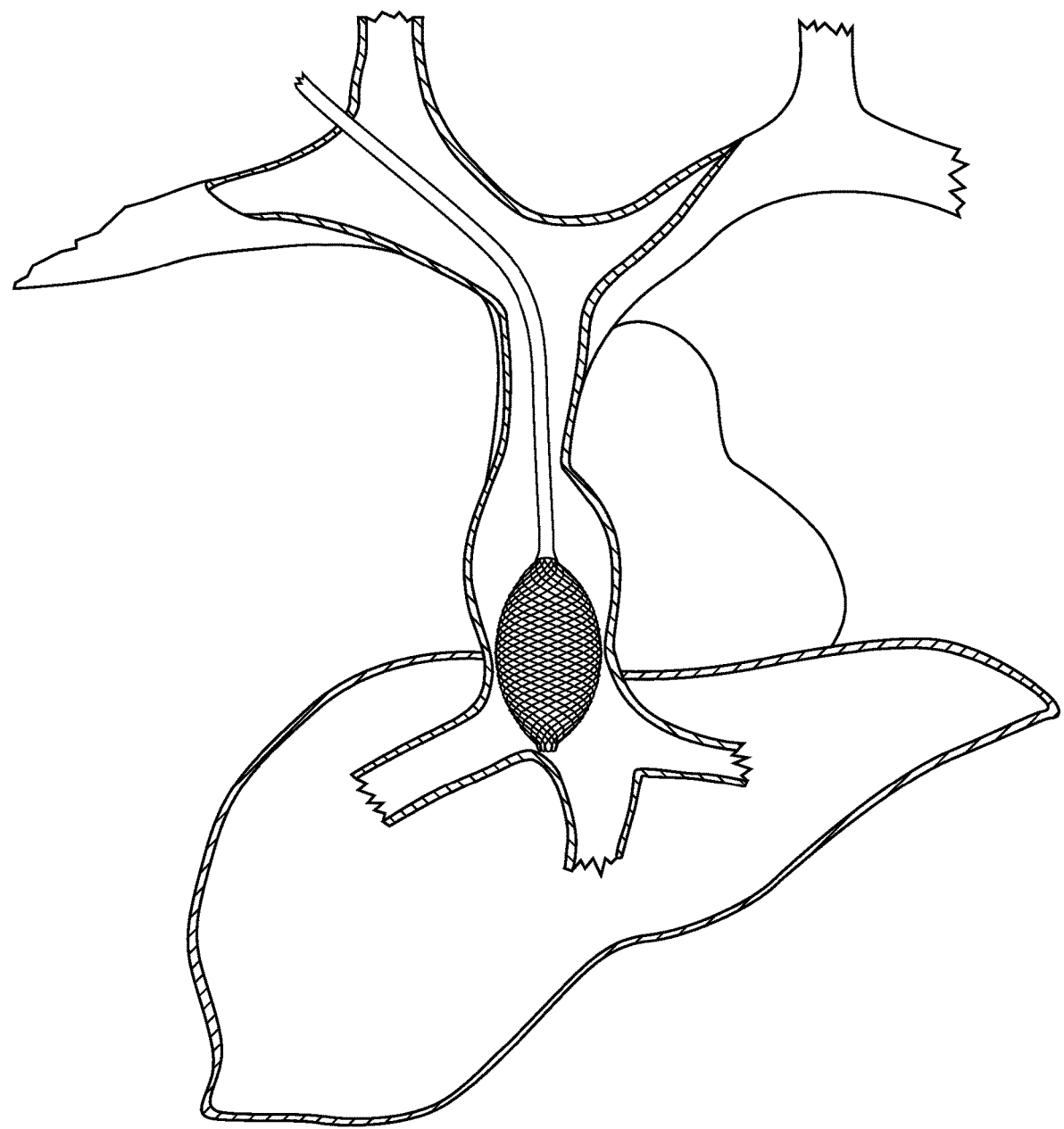
FIGS. 14A-14L illustrate various examples of positioned devices in different blood vessels.
Figure 14B:
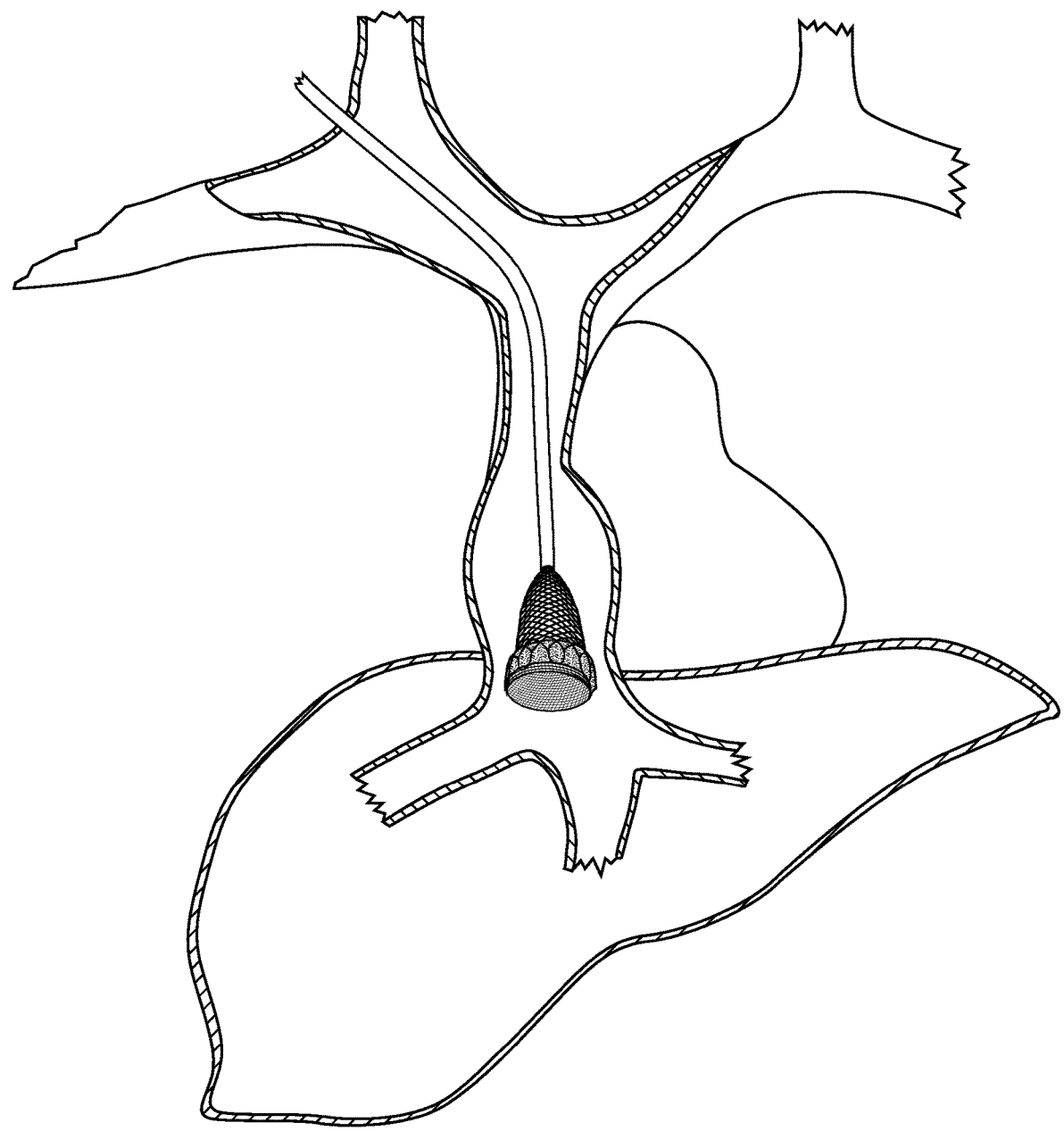
Figure 14C:
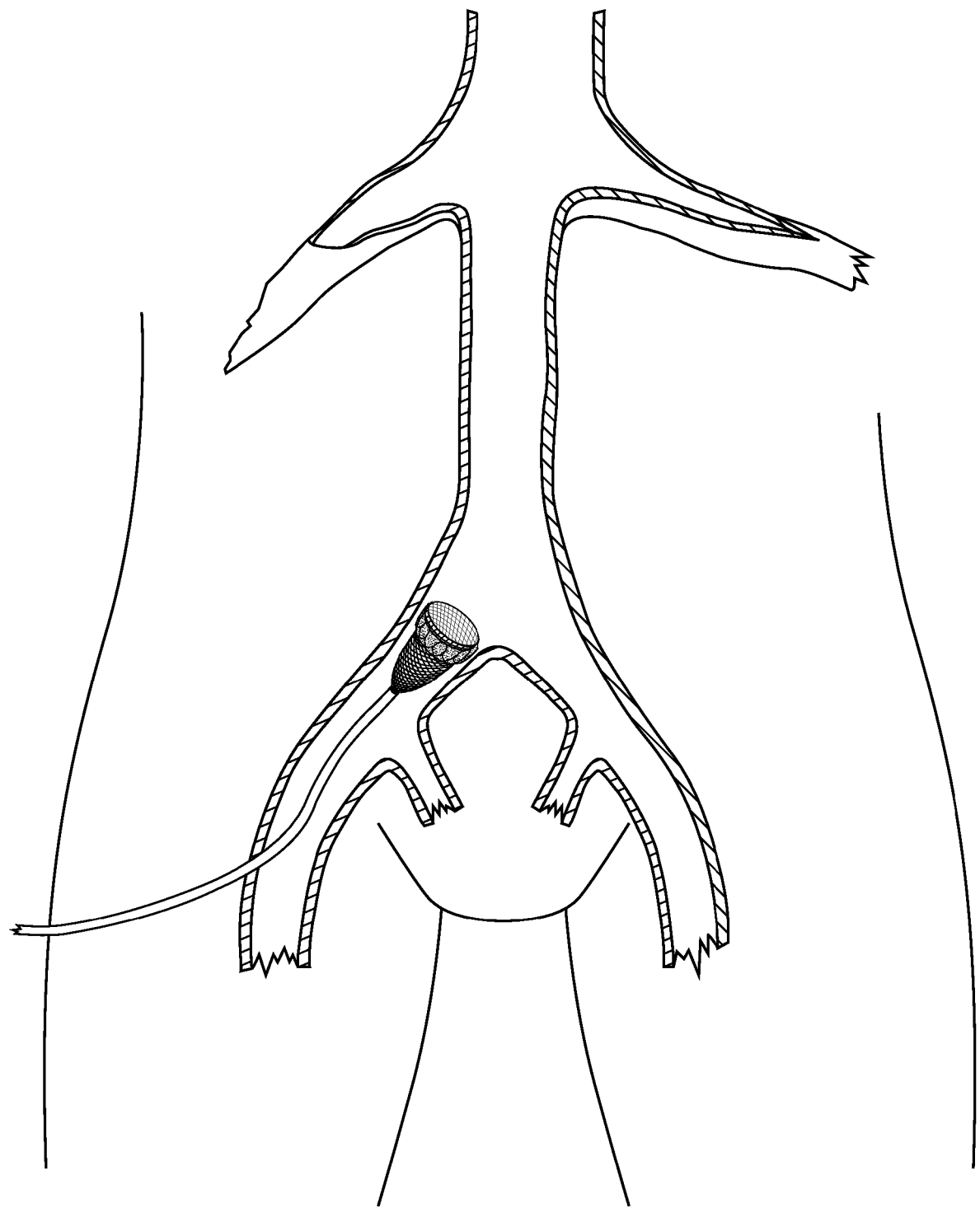
Figure 14D:
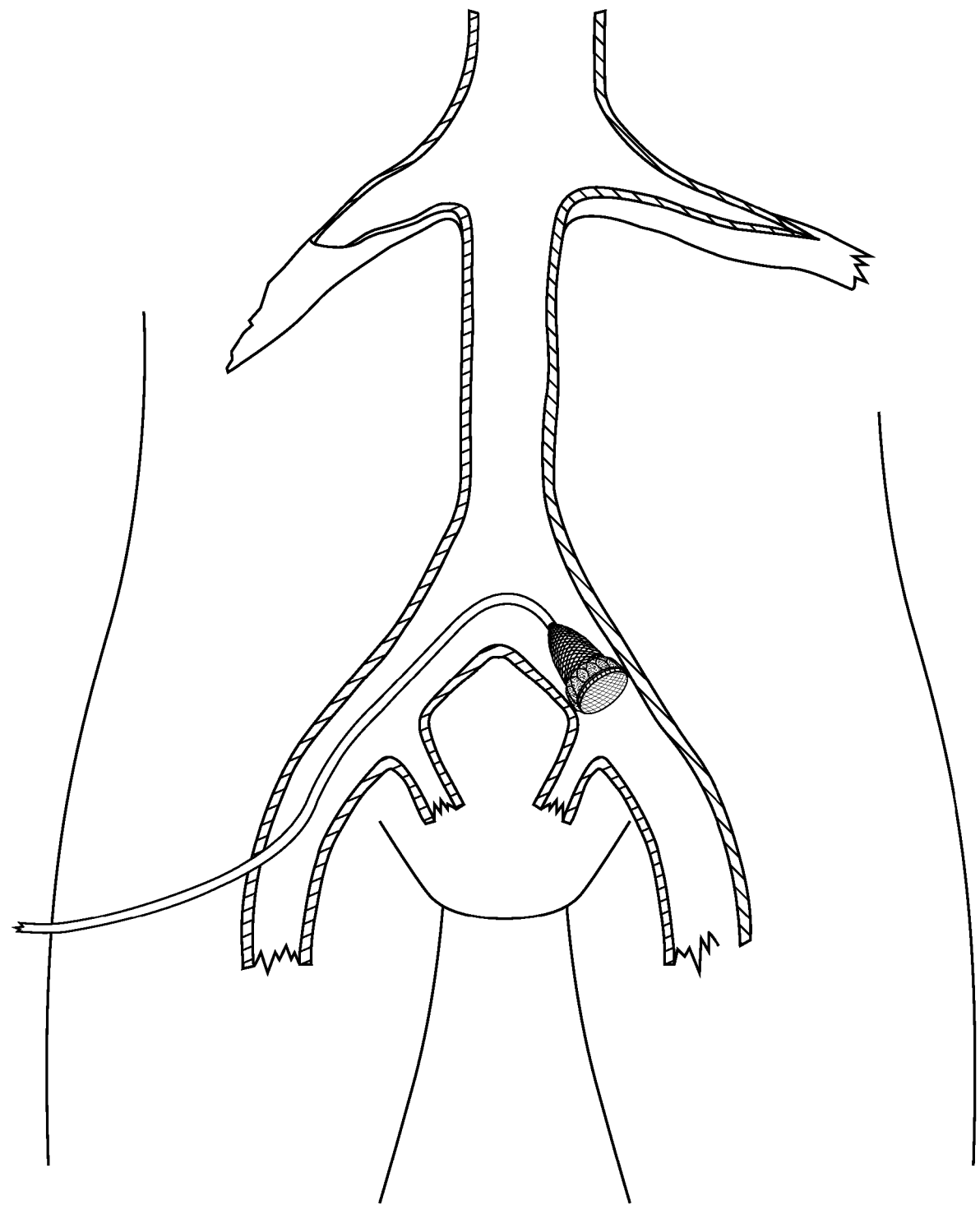
Figure 14E:
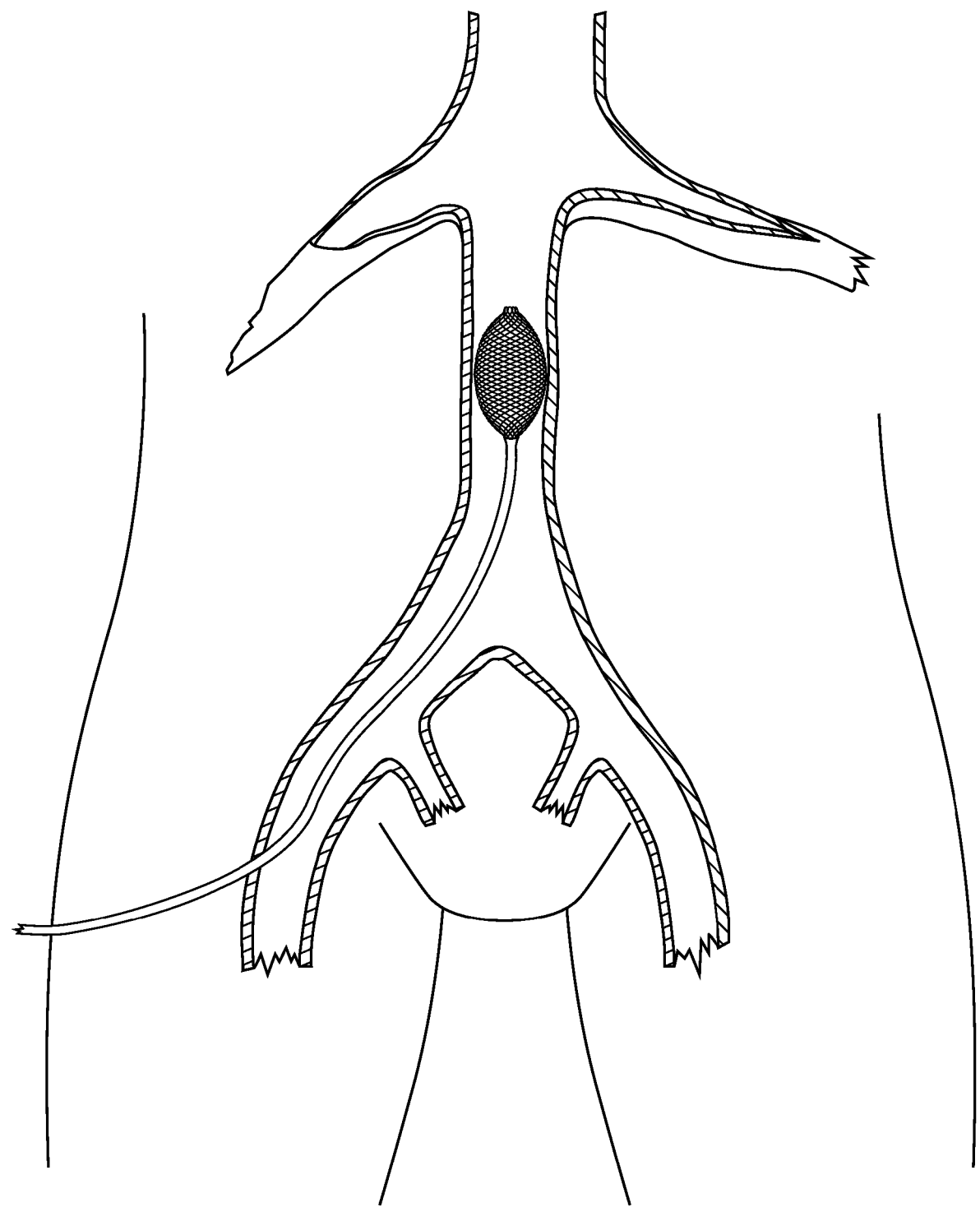
Figure 14F:
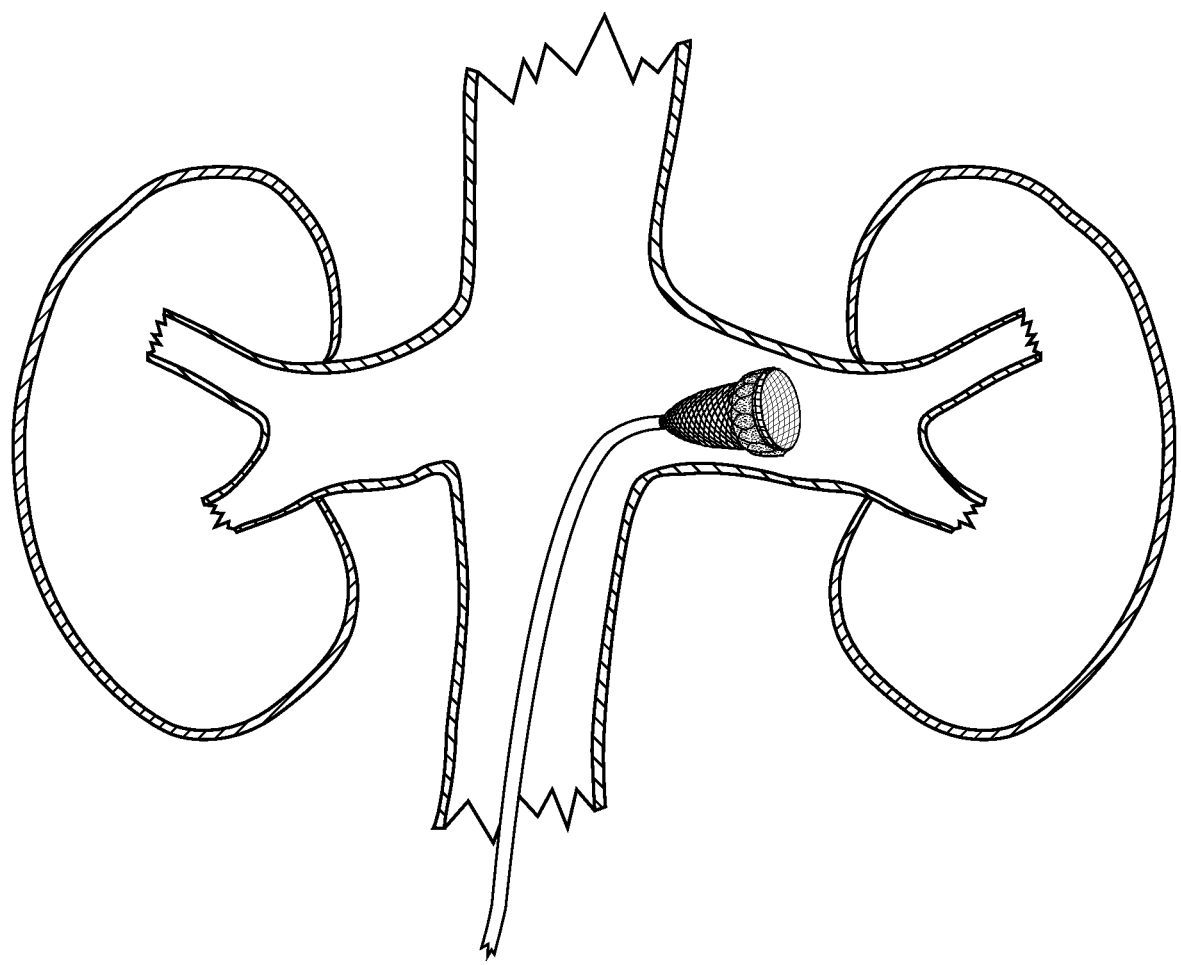
Figure 14G:
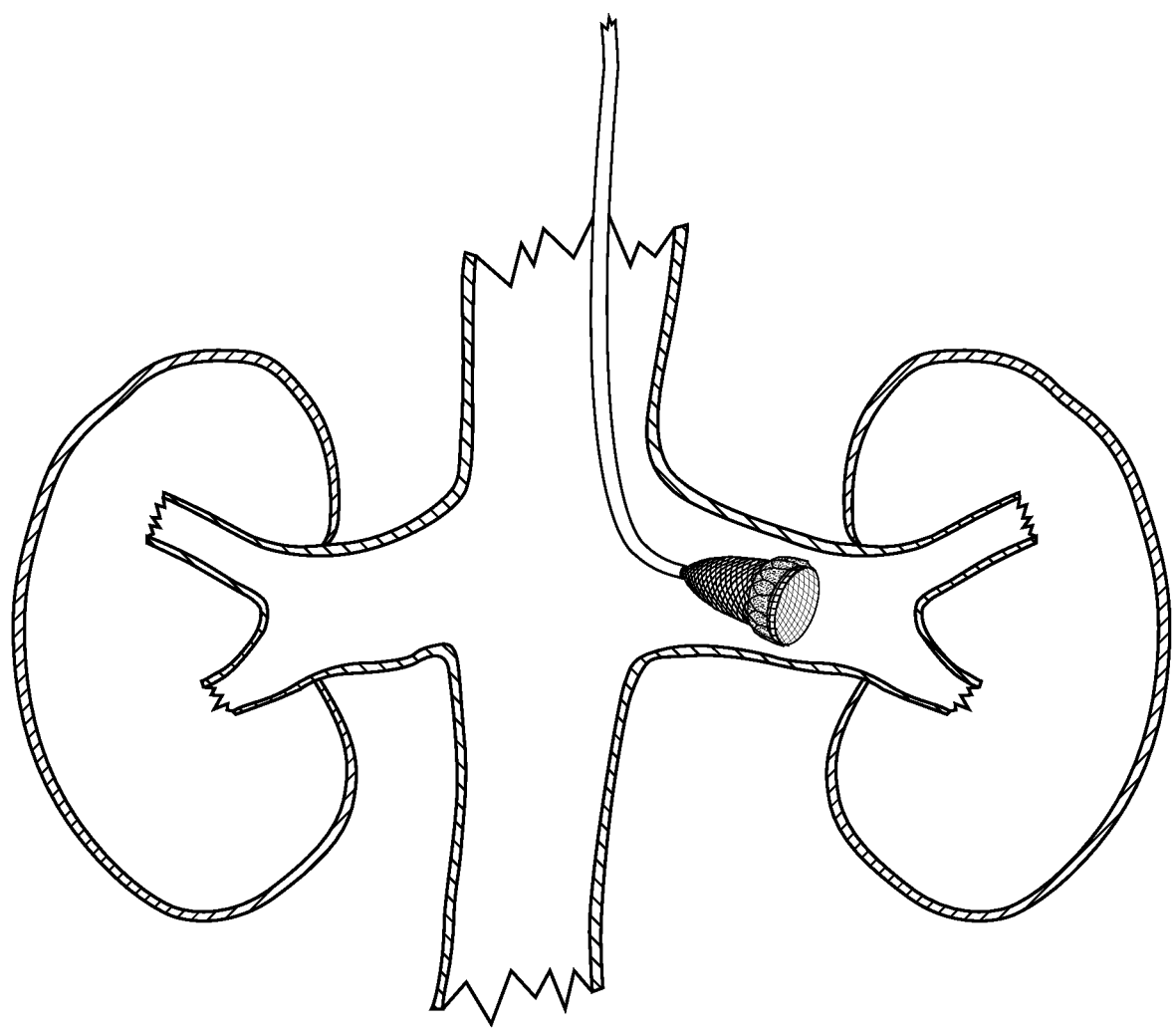
Figure 14H:
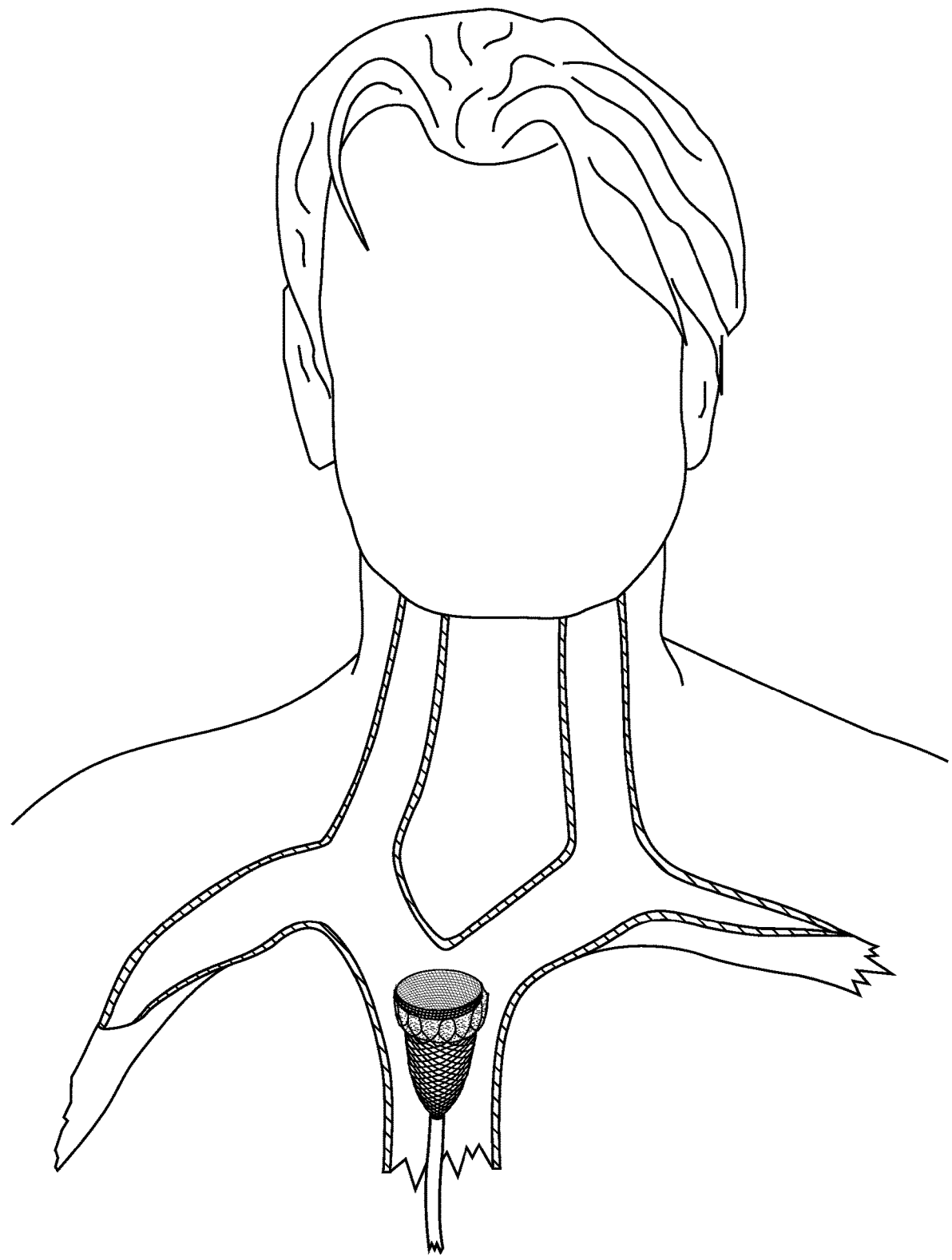
Figure 14I:
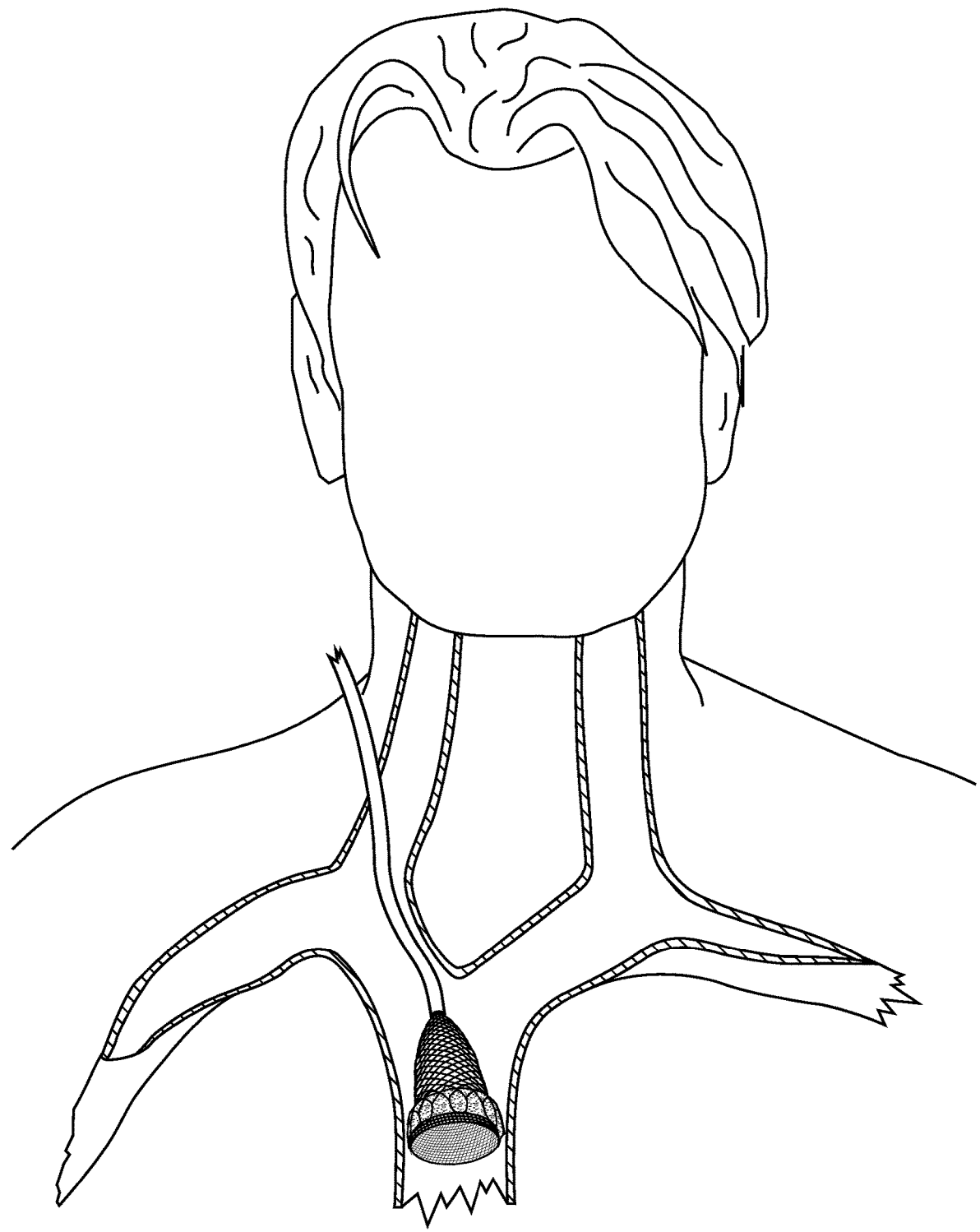
Figure 14J:
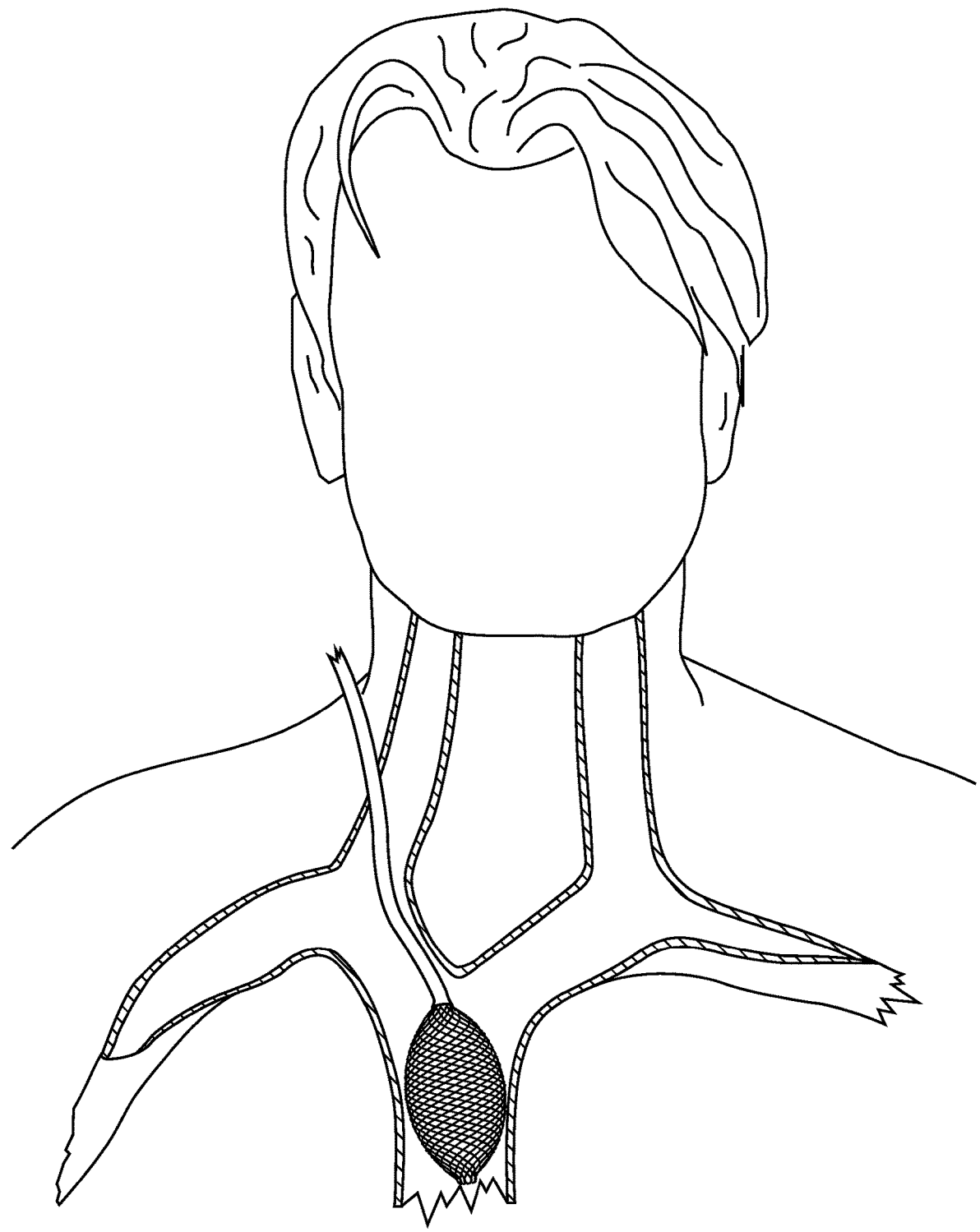
Figure 14K:
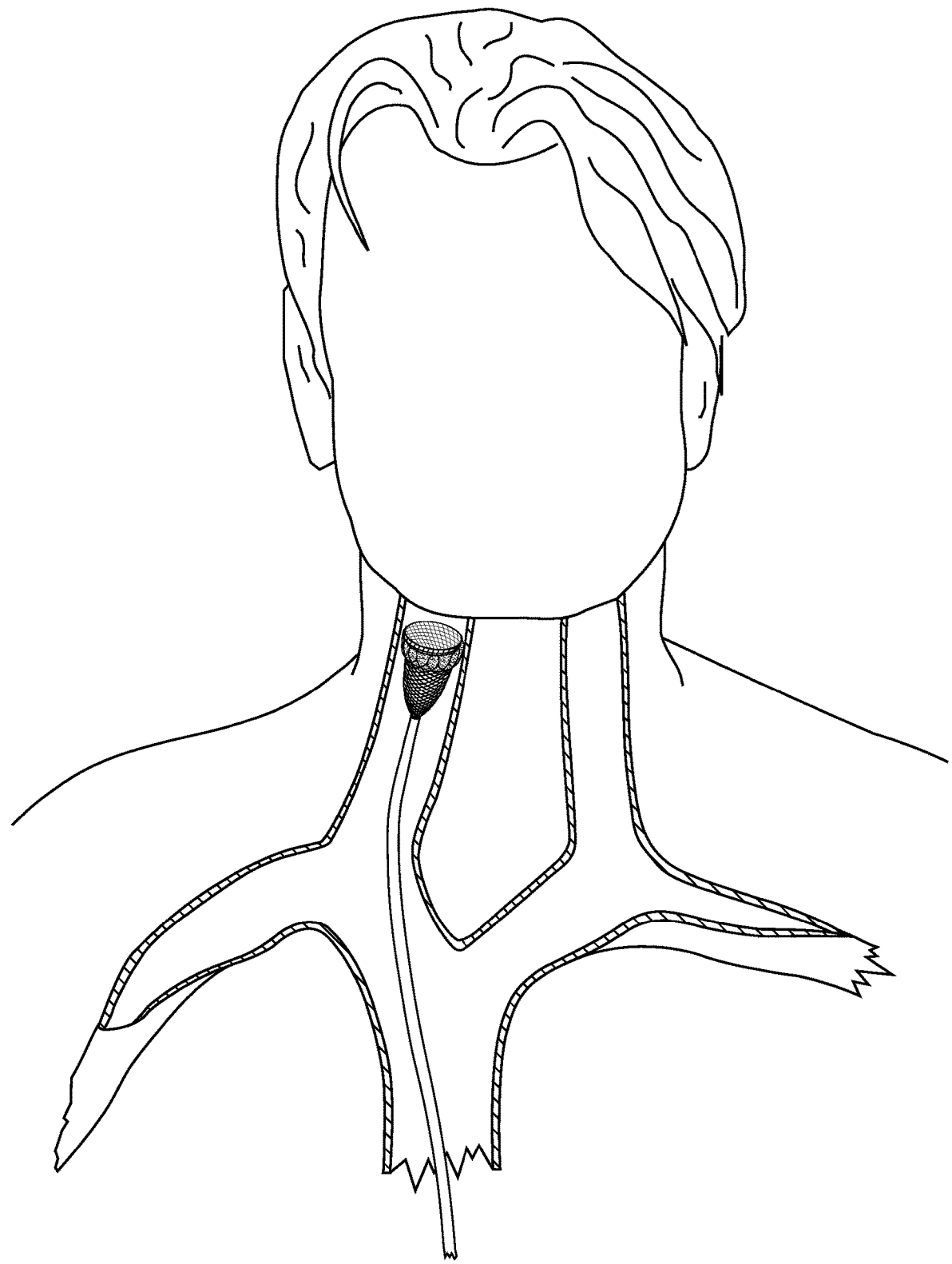
Figure 14L:
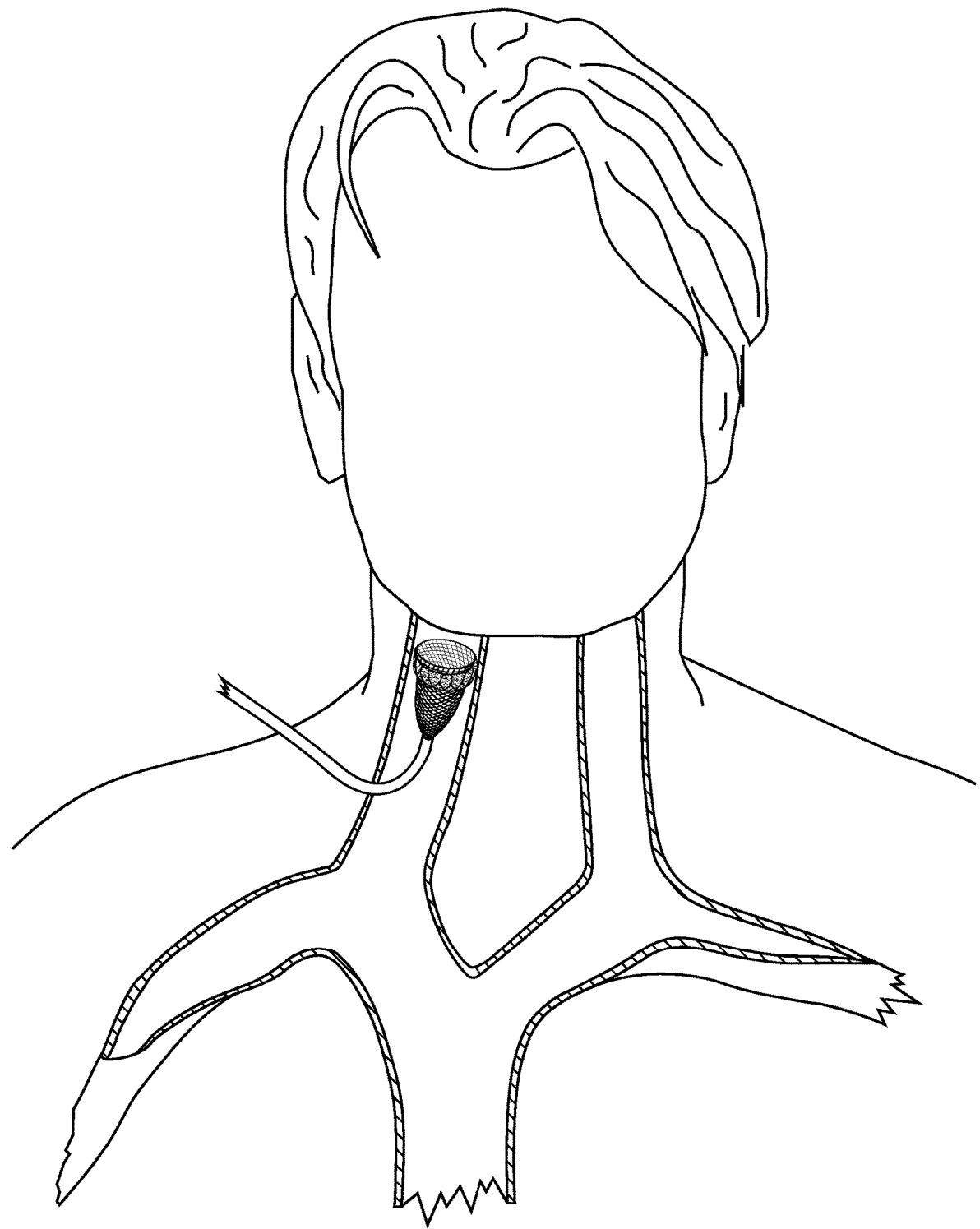

During extensive initial research of candidate compounds, nine materials were tested. Given interest in rapid high capacity drug binding, a metric referred to herein as TACE Factor (TF), was measured as total Dox bound during the first 10 minutes per ml of adsorbent with a goal TF being approximately 10 given a 2.5 ml constraint and aim to bind 25 mg of drug. One resin in particular, a macroporous strong acid ion-exchange resin with a hydrophilic polyvinyl backbone, demonstrated excellent results with a TF of 19 and rapid time to equilibrium essentially at 20 minutes. This is represented in the graph 1100 of FIG. 12, showing plots 1203 of Dox absorbed over time, with milligrams of Dox along axis 1201 and time in minutes along axis 1202. Biorad AG50W-X2 resin (e.g., 200-400 mesh) was used. 73% (49 or 67 mg Dox) was absorbed at 10 mins. A TF of 19 achieved. A generic equivalent resin, Dowex 50W-X2 (200-400 mesh) provided similar results. Another macroporous adsorbent resin without ion-exchange properties, also demonstrated similar results with a dramatic three-fold decrease in drug concentration over 60 minutes. This is represented in the graph 1300 of FIG. 13, showing plots 1303 of Dox concentration over time, with mg/ml of Dox shown along axis 1301 and time in minutes along axis 1302.

Preliminary device prototypes were also constructed a large stent device as well as a carotid protection filter. For instance, a partially deployed stent with 200-micron double mesh lining sandwiching adsorbent material. When deployed from its sheath within the selected vein, it has a conical shape or wind-sock like shape, with volume approximating that of a cone fitting within the renal vein (dimensions 6 cm length, 1.2 cm diameter).

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

The invention claimed is:

1. An in vivo filtration device positionable in a vein of a human or a non-human animal, the filtration device comprising:
   a catheter having a lumen;
   an elongated control member positioned within the lumen of the catheter,
   a filtration material disposed along an axis of the elongated control member within the lumen of the catheter, wherein the filtration material comprises resin beads within one or more porous membranes configured to adsorb or bind a chemotherapeutic agent administered in an artery supplying blood to an organ comprising a tumor, wherein the filtration device is dimensioned for positioning within the vein draining the blood from the organ in the human or non-human animal.

2. The filtration device of claim 1, wherein the resin adsorbs the chemotherapeutic agent.

3. The filtration device of claim 1, wherein the resin chemically binds the chemotherapeutic agent.

4. The filtration device of claim 1, wherein the resin is an ion exchange resin.

5. The filtration device of claim 1, wherein the resin is a strong acid cation polymer resin.

6. The filtration device of claim 1, wherein the resin comprises a polymeric adsorbent resin without ion exchange.

7. The filtration device of claim 1, wherein the resin includes sulfonate groups that ionically bind to the chemotherapeutic agent.

8. The filtration device of claim 1, wherein the resin is coated with heparin, polymethyl-methacrylate, or chitosan.

9. The filtration device of claim 1, wherein the elongated member is displaceable out a distal end of the catheter.

10. The filtration device of claim 1, wherein the filtration material is removable from the catheter while the catheter is positioned in the vein.

11. The filtration device of claim 1, wherein the chemotherapeutic agent is doxorubicin.

12. The filtration device of claim 1, wherein the catheter has a diameter of 8 mm-14 mm or 22 mm-30 mm.

13. The filtration device of claim 1, wherein the one or more porous membranes comprise a porous membrane shaped to increase and then decrease in cross-sectional area from a distal end to a proximal end.

14. The filtration device of claim 1, wherein the one or more porous membranes comprise a porous membrane that is expandable to occupy a cross sectional area of the vein within which the porous membrane is deployed.

15. The filtration device of claim 14, wherein the porous membrane is biased to an expanded state so that when the porous membrane is displaced outside the catheter, the porous membrane is expanded to occupy the cross sectional area of the vein.

16. An in vivo positionable filtration device for filtering a chemotherapeutic agent in blood flowing in a blood vessel, the filtration device comprising:

an elongated control member comprising a distal end; and a filtering component carried on the distal end of the elongated control member comprising:

a porous membrane comprising a proximal end and a distal end, the porous membrane shaped to increase and then decrease in cross-sectional area from the distal end of the porous membrane to the proximal end of the porous membrane, the porous membrane configured to be deployed within the blood vessel such that the blood flowing through the blood vessel passes through an interior of the filtering component; and filtration material comprising a plurality of beads disposed within the porous membrane configured to bind the chemotherapeutic agent to the beads as the blood flows through the interior of the filtering component.

17. The device of claim 16, wherein the beads comprise material configured to adsorb the chemotherapeutic agent.

18. The device of claim 16, wherein the beads comprise ion exchange resin.

19. The device of claim 18, wherein the resin is a strong acid cation exchange polymer resin.

20. An in vivo positionable filtration device for filtering a chemotherapeutic agent in blood flowing in a blood vessel, the filtration device comprising:

an elongated member comprising a distal end; and a filtering component carried on the distal end of the elongated member comprising:

a porous membrane comprising a proximal end and a distal end, the porous membrane expandable when deployed within the blood vessel to occupy a cross sectional area of the blood vessel within which the porous membrane is deployed such that the blood flowing through the blood vessel passes through an interior of the filtering component; and filtration material comprising a plurality of beads disposed within the porous membrane configured to bind or adsorb the chemotherapeutic agent to the beads as the blood flows through the interior of the filtering component.

\* \* \* \* \*